US006462070B1

(12) United States Patent
Hasan et al.

(10) Patent No.: US 6,462,070 B1
(45) Date of Patent: Oct. 8, 2002

(54) PHOTOSENSITIZER CONJUGATES FOR PATHOGEN TARGETING

(75) Inventors: Tayyaba Hasan, Arlington; Michael R. Hamblin; Nikos Soukos, both of Revere, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/812,606

(22) Filed: Mar. 6, 1997

(51) Int. Cl.[7] .................... A61K 37/18; A61K 38/00; A61K 31/40

(52) U.S. Cl. ..................... 514/410; 514/2; 514/12; 514/14

(58) Field of Search ................ 514/2, 12, 14, 514/410

(56) References Cited

U.S. PATENT DOCUMENTS

| 5,096,815 A | 3/1992 | Ladner et al. ............. 435/69.1 |
| 5,198,346 A | 3/1993 | Ladner et al. ............. 435/69.1 |
| 5,223,409 A | 6/1993 | Ladner et al. ............. 435/69.7 |
| 5,486,503 A | 1/1996 | Oppenheim et al. .......... 514/2 |

FOREIGN PATENT DOCUMENTS

WO    WO 88/06630    9/1988

OTHER PUBLICATIONS

Colon et al, J Dent. Res 72 (LADR Abstracts) abstract No. 1751, 1993.*
Hasan et al, Proceedings of AACR vol. 28, abstract No. 1568 Mar. 1987, Jan. 1987.*
Fomichev et al, 115CA:227138, 1991.*
Shima et al, 102CA:75536, 1993.*
Charbit, A. et al. (1986). Probing the topology of a bacterial membrane protein by genetic insertion of a foreign epitope; expression at the cell surface. *The EMBO Journal,* 5 (11), 3029–3037.
Colon, J.O. et al. (1993). Bactericidal effect of salivary histatin 5 on *porphyromonas gingivalis. J. Dent. Res.* 72, 322, Abstract No. 1751.
Cull, M.G. (1992). Screening for receptor ligands using large libraries of peptides linked to the C terminus of the lac repressor. *Proc. Natl. Acad. Sci. USA 89,* 1865–1869.
Cunningham, B.C. and J.A. Wells. (1989). High–resolution eptitope mapping of hGH–receptor interactions by alanine–scanning mutagenesis. *Science,* 244, 1081–1085.
Cwirla, S.E. et al. (1990). Peptides on phage: a vast library of peptides for identifying ligands. *Proc. Natl. Acad. Sci. USA 87,* 6378–6382.
Devlin, J.J. et al. (1990). Random peptide libraries: a source of specific protein binding molecules. *Science 249,* 404–406.

Dobson, J. and M. Wilson. (1992). Sensitization of oral bacteria in biofilms to killing by light from a low–power laser. *Archs. Oral Biol. 37* (11) 883–887.
Emancipator, K. et al. (1992). In vitro inactivation of bacterial endotoxin by human lipoproteins and apolipoproteins. *Infection and Immunity 60* (2): 596–601.
Fuchs, P. et al. (1991). Targeting recombinant antibodies to the surface of *Escherichia coli*: fusion to a peptidoglycan associated lipoprotein. *Bio/Technology 9,* 1369–1372.
Gallop, M.A. et al. (1994). Applications of combinatorial technologies to drug discovery. 1. Background and peptide combinatorial libraries. *J. Med. Chem. 37* (9), 1233–1251.
Hansson, M. et al. (1992). Expression of recombinant proteins on the surface of the coagulase–negative bacterium *Staphylococcus xyllosus. Journal of Bacteriology 174* (13), 4239–4245.
Hasan, T. et al. (1987). Site–specific conjugation of chlorine–$e_6$ to an anti–bladder carcinoma monoclonal antibody and laser–induced selective cytotoxicity of the conjugate. Proceedings of AACR 28, 395, Abstract No. 1568.
Jack, R.W. et al. (1995). Bacteriocins of gram–positive bacteria. *Microbiol Rev. 59* (2), 171–200.
Kalpidis, C.D. et al. (1992). Effects on human salivary histatin 5 on Actinomyces species. *J Dent Res 71* (AADR Abstracts) 305, Abstract No. 1595.
Klauser, T et al. (1990). Extracellular transport of cholera toxin B subunit using Neisseria IgA protease β–domain: Conformation–dependent outer membrane translocation. *The EMBO Journal 9* (6), 1991–1999.
Lambert, C.R. et al. (1986). The effects of porphyrin structure and aggregation state on photosensitized processes in aqueous and micellar media. *Photochemistry and Photobiology 44* (5), 595–601.
Liu, W. and J.N. Hansen. (1992). Enhancement of the chemical and antimicrobial properties of subtillin by site–directed mutagenesis. *J. Biol. Chem. 267* (35), 25078–25085.
Murakami, Y. et al. (1990). Inhibitory effects of synthetic histidine–rich peptides on heamagglutination by bacterioides gingivalis 381. *Archs. Oral Biol. 35* (9), 775–777.
Netea, M.G. et al. (1996). Low–density lipoprotein receptor–deficient mice are protected against lethal endotoxemia and severe gram–negative infections. *J. Clin. Invest. 97* (6), 1366–1372.
Okamoto, H. et al. (1992). Dye–mediated bactericidal effect of He–Ne laser irradiation on oral microorganisms. *Lasers in Surgery and Medicine 12,* 450–458.
Roberts, B.L. et al. (1992). Directed evolution of a protein: Selection of potent neutorphil elastase inhibitors displayed on M13 fusion phage. *Proc. Natl. Acad. Sci. USA 89,* 2429–2433.

(List continued on next page.)

Primary Examiner—Russell Travers
(74) *Attorney, Agent, or Firm*—Frommer Lawrence & Haug LLP; Thomas J. Kowalski; Amy Leahy

(57) ABSTRACT

Conjugate molecules which include photosensitizer compositions conjugated to non-antibody non-affinity pair targeting moieties and methods of making and using such conjugates are described.

5 Claims, 11 Drawing Sheets

OTHER PUBLICATIONS

Russell, D.A. et al. (1991). A comparison of fluorescence excitation sources for in vivo pharmacokinetic measurements of the photdynamic therapy model photosensitizer hematoporphyrin IX. *Canadian Journal of Applied Spectroscopy 36* (5), 103–107.

Saberwal, G. and R. Nagaraj. (1994). Cell–lytic and antibacterial peptides that act by perturbing the barrier function of membranes : facet of their conformational features, structure–function correlations and membrane–perturbing abilities. *Biochimica et Biophysica Acta 1197*, 109–131.

Scott, J.K. & G.P. Smith. (1990). Searching for peptide ligands with an epitope library. *Science 249*, 386–390.

Shai, Y. et al. (1990). Channel formation properties of synthetic pardaxin and analogues. *J. Biol. Chem. 256* (33), 20202–20209.

Thiry, G. et al. (1989). Cloning of DNA sequences encoding foreign peptides and their expression in the K88 Pili. *Applied and Environmental Microbiology 55* (4), 984–993.

Westerhoff, H.V. et al. (1989). Magainins and the disruption of membrane–linked free–energy transduction. *Proc. Natl. Acad. Sci. USA 86*, 6597–6601.

Wilson, M. (1994). Bactericidal effect of laser light and its potential use in the treatment of plaque–related diseases. *International Dental Journal 44*, 181–189.

Wilson, M. (1993). Photolysis of oral bacteria and its potential use in the treatment of caries and periodontal disease. *Journal of Applied Bacteriology 75*, 299–306.

Wilson, M. et al. (1993). Sensitization of periodontopathogenic bacteria to killing by light from of a low–power laser. *Oral Microbiol. Immunol. 8*, 182–187.

Wilson, M. et al. (1993). Sensitization of oral bacteria to killing by low–power laser radiation. *Current Microbiology 25*, 77–81.

Wurfel, M.M. et al. (1995). Soluble CD14 acts as a shuttle in the neutralization of lipopolysaccharide (LPS) by LPS-binding protein and reconstituted high density lipoprotein. *J. Exp. Med. 181*, 1743–1754.

Yang, R. et al. (1992). Novel method to extract large amounts of bacteriocins from lactic acid bacteria. *Applied and Environmental Microbiology 58* (10), 3355–3359.

Maier et al., "Preparation of mesotetraphenylporphyrin complexes as diagnostic . . . " Ger Offen. DE 4,305,523, Aug. 18, 1994, vol. 122, Abstract No. 160040d.

Sakata et al., "Preparation of porphyrin compounds as photosensitizers for . . . " Jp 0597,85, Apr. 20, 1993, vol. 119, Abstract No. 203241c.

Malik et al., "New Trends in Photobiology (Invited Review) Bactericidal Effects of Photoactivated Porphyrins—An Alternative Approach to Antimicrobial Drugs" Journal of Photochemistry and Photobiology, B: Biology, 5 (1990) 281–293.

* cited by examiner

Gly-Tyr-Lys-Arg-Lys-Phe-His-Glu-Lys-His-His-Ser-His-Arg-Gly-Tyr

VIII

↓ 6

Gly-Tyr-Lys-Arg-Lys-Phe-His-Glu-Lys-His-His-Ser-His-Arg-Gly-Tyr

IX

↓ 7

Gly-Tyr-Lys-Arg-Lys-Phe-His-Glu-Lys-His-His-Ser-His-Arg-Gly-Tyr

X

PHOTOSENSITIZER CONJUGATES FOR PATHOGEN TARGETING

GOVERNMENT FUNDING

This invention was made with government support from the National Institutes of Health grant NIH RO1 AR40352 and from the Office of Naval Research. The government has certain rights in the invention.

FIELD OF THE INVENTION

The invention relates to a conjugate which includes a photosensitizer and a targeting moiety, and methods of using the conjugate.

BACKGROUND OF THE INVENTION

Infectious diseases remain an unsolved problem, due largely to emergence of multiply-antibiotic resistant strains of bacteria, newly discovered viral diseases, and the spread of fungal and protozoan diseases.

Advanced periodontal disease is one of a large number of oral infectious diseases, and is the principal cause of tooth loss in those over 30 years old. Periodontal diseases arise from the interaction between bacterial cells and their products in dental plaque, and the host defense mechanisms (Antczak-Bouckoms, A., (1994), *J. Dent. Educ.* 58:625–640). Current treatments often rely on mechanical removal of the plaque and bacteria, which can be inefficient (Unsal E. et al., (1995), *J. Periodontol.* 66:47–51), or antibiotic therapy, which can lead to bacterial resistance (Olsvik, B. et al., (1995), *J. Clin. Periodontol.* 22:391–396).

Photodynamic therapy (PDT) has been proposed as an attractive method of eliminating oral bacteria and bacteria in topical and gastrointestinal infections because these sites are relatively accessible to illumination. For example, fiber optics can be used to deliver light into the dental pocket (Wilson, M., (1993), *J. Appl. Bacteriol.* 75:299–306).

SUMMARY OF THE INVENTION

The inventor has discovered that classes of molecules not hither to used as targeting moieties for photosensitizers, can be used to target photosensitizers.

Accordingly, the invention features, a conjugate molecule which includes a photosensitizer coupled to a non-pair member (NPM) moiety, e.g., an NPM-polypeptide.

In embodiments in which the targeting moiety includes a polypeptide, the targeting moiety can be a linear, branched, or cyclic polypeptide.

In preferred embodiments, the targeting moiety includes a small anti-microbial peptide (SAMP). Histatins, defensins, cecropins, magainins, Gram positive bacteriocins, and peptide antibiotics can be SAMP's. In preferred embodiments, the targeting moiety includes a bacterial, fungal, animal, e.g., mammalian, e.g., human, SAMP, or an active fragment or analog thereof.

In preferred embodiments the targeting moiety includes a defensin, or an active fragment or analog thereof. By way of example the defensin can be: a human defensin, e.g., HNP-1, -2, -3, or -4; a guinea pig defensin, e.g., GPNP; a rabbit defensin, e.g., rabbit NP-1, -2, -3A, -3B, or 5; a rat defensin, e.g., rat NP-1, -2, -3, or -4; murine cryptin; bovine granulocyte bactenecin or indolicidin; or bovine seminal plasmin.

In preferred embodiments, the targeting moiety includes a SAMP of insect origin, or an active fragment or analog thereof, e.g., a cecropin from Cecropia moths, bumble bees, fruit flies, or other insects, an apidaecin from honeybees, or an adropin from fruit flies.

In preferred embodiments, the targeting moiety includes a SAMP of amphibial origin, or an active fragment or analog thereof, e.g., a magainin, a PGLA, a XPF, a LPF, a CPG, a PGQ, a bombinin, a bombinin-like peptide BLP-1, -2, -3, or -4, or a brevinin.

In preferred embodiments the targeting moiety includes a SAMP from an invertebrate, or an active fragment, or analog thereof, e.g., tachyplesin I, II, or III, or polyphemusin I or II, from horseshoe crab. In preferred embodiments, the targeting moiety is from a fish, e.g., pardaxin.

In preferred embodiments, the targeting moiety includes a bacteriocin, more preferably a Gram positive bacteriocin, or an active fragment, or analog thereof, e.g., a nisin, a subtilin, epidermin, gallidermin, salivarin, or a lacticin.

In preferred embodiments, the targeting moiety includes a peptide antibiotic, or an active fragment or analog thereof, e.g., a tyrocidin, or a bacitracin.

In preferred embodiments the targeting moiety includes a histatin, or an active fragment or analog thereof, e.g., histatin-1 through -8, preferably histatin-1, -3, or -5. In preferred embodiments the targeting moiety includes histatin-5 residues 13–24, or corresponding residues from other histatins. In preferred embodiments the targeting moiety includes a histatin molecule which has been engineered to include an internal duplication.

In preferred embodiments, the targeting moiety includes a polypeptide having an affinity for a polysaccharide target, e.g., a lectin. By way of example the lectin can be a seed, bean, root, bark, seaweed, fungal, bacteria, or invertebrate lectin. In preferred embodiments, the targeting moiety includes a plant polypeptide, e.g., a lectin from jack bean, e.g., concanavalin A, or a lectin from a lentil, *Lens culinaris*.

In preferred embodiments, the targeting moiety includes a salivary polypeptide, or an active fragment or analog thereof. Examples of salivary polypeptides are the histatins, e.g., histatin-1 through -8, or more preferably, histatin-1, -3, or -5. In preferred embodiments the targeting moiety includes histatin-5 residues 13–24, or corresponding residues from other histatins. In preferred embodiments the targeting moiety includes a histatin molecule which has been engineered to include an internal duplication.

In preferred embodiments, the targeting moiety includes a Gram negative bacteriocin, e.g., colicin B, colicin E1, or colicin Ia.

In preferred embodiments the targeting moiety includes bacterially elaborated polypeptide, e.g., nisin, subtilin, epidermin, gallidermin, salivarin, or lacticin.

In preferred embodiments the targeting moiety includes a molecule, e.g., a peptide, other than an antibody or either member of a receptor-ligand pair.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

In preferred embodiments the targeting moiety includes a peptide in which at least 10, 20, 30, 40, 50, 60, 70, 80, 90% of the amino acid residues are of one amino acid residue, e.g., a positively charged amino acid residue, e.g., a lysine reside, an arginine residue, or an ornithine residue. Particularly preferred targeting moieties are polyamino acids, e.g., polylysine, polyarginine, or polyornithine.

In preferred embodiments the targeting moiety: is cationic; has a net positive charge of +1, +2 or +3 per molecule;

has a net positive charge equal to or greater than +4; includes a positively charged amino acid residue, e.g, lysine; includes at least 2, 3, 4, or more positively charged amino acid residues, e.g., a lysine, arginine, or ornithine residue.

In other embodiments the targeting moiety: is anionic; has a net negative charge of -1, -2 or -3 per molecule; has a net negative charge equal to or greater than -4; includes a negatively charged amino acid residue, e.g., aspartic acid or glutamic acid; includes at least 2, 3, 4, or more negatively charged amino acid residues, e.g, glutamic; includes at least 10, 20, 30, 40, or 50% or more negatively charged amino acid residues, e.g. aspartic acid, or glutamic acid.

In preferred embodiments the targeting moiety: is approximately neutral in charge; includes at least 50, 60, 70, 80, or 90% amino acid residues which are neutral amino acid residues, such as serine, threonine, alanine, methionine, cysteine, or valine.

In preferred embodiments the targeting moiety has a molecular weight of more than 1200, 1800, 2400, 3000, 6000, 10,000, 25,000, 50,000, 100,000, or 200,000 daltons. In preferred embodiments the targeting moiety has a molecular weight of less than 250,000, 150,000, 60,000, 25,000, 10,000, 8,000, or 6,000 daltons. In particularly preferred embodiments the molecular weight of the targeting moiety is between 300 and 1800, 600 and 2400, 1200 and 6,000, 5,000 and 8,000, 8,000 and 15,000, 15,000 and 30,000, 35,000 and 70,000, 70,000 and 150,000, or 150,000 and 300,000 daltons.

In preferred embodiments the targeting moiety includes a peptide at least 3, 6, 12, 18, 24, 30, 60, 100, 250, 500, 1,000, or 2,500 residues in length. In preferred embodiments the targeting moiety is a peptide less than 3,000, 1,500, 700, 300, 150, 100, 80, 60,40, 30, or 15 residues in length. In particularly preferred embodiments the targeting moiety includes a peptide of between 6 and 15, 12 and 18, 18 and 30, 20 and 40, 30 and 60, 80 and 120, 150 and 300, 300 and 600, 800 and 1,200, or 2,000 and 3,000 residues in length.

In preferred embodiments the targeting moiety includes a protein which forms a pore in the permeability barrier of the target organism, e.g., in *Staphylococcus aureus, Klebsiella pneumoniae, Candida albicans, Leishmania donovani,* or *Giardia lamblia.*

In other preferred embodiments, the targeting moiety includes a low density lipoprotein, a high density lipoprotein or a very low density lipoprotein.

In preferred embodiments, the targeting moiety has been selected using a surface molecule of the target organism as an affinity selection or screen, e,g, the targeting moiety has been selected in a chemical or phage display library.

In particularly preferred embodiments the targeting moiety includes a polylysine molecule. The polylysine can be between 6 and 15, 12 and 18, 18 and 30, 20 and 40, 30 and 60, 80 and 120, 150 and 300, 300 and 600, 800 and 1,200, or 2,000 and 3,000 residues in length.

In preferred embodiments the targeting moiety includes a polypeptide, e.g., a polyamino acid, which has been chemically modified to alter its charge, e.g., the charge of side chains of one or more amino acid residues of the polyamino acid. For example, one or more, or approximately 10, 25, 50, 75, 90 or 100% of the charged side chains can be modified. By modified is meant that a negative side chain, e.g., a glutamic acid, or an aspartic acid, side chain is made positive or neutral in charge, a positively charged side chain, e.g., the side chain of lysine, arginine, or ornithine is made negative or neutral in charge. By way of example, one or more of the side chains of polylysine can be made neutral or negative in charge.

In preferred embodiments: the photosensitizer produces singlet oxygen upon absorption of electromagnetic irradiation at the proper energy level and wavelength; the photosensitizer includes a porphyrin or porphyrin derivative; the photosensitizer includes chlorin e6 or a chlorin derivative.

In preferred embodiments the conjugate further includes a backbone member. In such embodiments the backbone is coupled both to a photosensitizer and to a targeting moiety. The backbone can itself also be a targeting moiety, e.g. polylysine.

In preferred embodiments, the conjugate molecule has affinity for a target organism. The target organism, by way of example, can be: a microorganism, e.g., a bacterial cell, a fungal cell, a protozoan cell, a cell of *Pneumocystis carinii;* a virus; or, a parasitic helminth; or an arthropod.

In preferred embodiments where the cell is a bacterial cell, the bacterial cell can be a Staphylococcus, Streptococcus, Enterococcus, Mycobacterium, Pseudomonas, Salmonella, Shigella, Escherichia, Erwinia, Klebsiella, Borrelia, Treponema, Campylobacter, Helicobacter, Bordetella, Neisseria, Legionella, Leptospira, Serpulina, Mycoplasma, Bacteroides, Klebsiella, Yersinia, Chlamydia, Vibrio, Actinobacillus, Porphyria, Hemophilus, Pasteurella, Peptostreptococcus, Listeria, Propionibacterium, Mycobacterium, Corynebacterium or Dermatophilus cell.

In preferred embodiments where the cell is a fungal cell, the cell can be a Candida or an Aspergillus cell.

In preferred embodiments, the organism is *Pneumocystis carinii.*

In preferred embodiments where the target organism is a protozoan cell, the cell is an Entamoeba, a Toxoplasma, a Giardia, a Leishmania, a Crytosporidium, or a Schistosoma.

In preferred embodiments where the target organism is a virus, the virus is an HIV, an HTLV, a hepatitis virus, an influenza virus, a rhinovirus, a papilloma virus, a measles virus, a Herpes virus, a rotavirus, a parvovirus, a psittacosis virus, or an Ebola virus.

In preferred embodiments where the target organism is an arthropod, the arthropod is a parasitic mite.

In preferred embodiments where the target organism is a helminth, the helminth is a nematode or a trematode.

In preferred embodiments the target organism is an oral bacterial species, e.g., *Porphyromonas (Bacteroides) gingivalis.*

In another aspect, the invention features a conjugate molecule which includes a photosensitizer coupled to a non-pair member (NPM) targeting moiety and a pharmaceutically acceptable carrier.

In another aspect, the invention features, a conjugate molecule which includes a photosensitizer coupled to a targeting moiety which includes a non-pair member (NPM) polypeptide moiety having affinity for an oral bacterial species.

In embodiments in which the targeting moiety includes a polypeptide, the targeting moiety can be a linear, branched, or cyclic polypeptide.

In particularly preferred embodiments the targeting moiety includes a polylysine molecule. The polylysine can be between 6 and 15, 12 and 18, 18 and 30, 20 and 40, 30 and 60, 80 and 120, 150 and 300, 300 and 600, 800 and 1,200, or 2,000 and 3,000 residues in length.

In preferred embodiments the targeting moiety includes a polypeptide, e.g., a polyamino acid, which has been chemically modified to alter its charge, e.g., the charge of side chains of one or more amino acid residues of the polyamino acid. For example, one or more, or approximately 10, 25, 50, 75, 90 or 100% of the charged side cains can be modified. By modified is meant that a negative side chain, e.g., a glutamic acid, or an aspartic acid, side chain is made positive or neutral in charge, a positively charged side chain, e.g., the side chain of lysine, arginine, or ornithine is made negative or neutral in charge. By way of example, one or more of the side chains of polylysine can be made neutral or negative in charge.

In preferred embodiments: the photosensitizer produces singlet oxygen upon absorption of electromagnetic irradiation at the proper energy level and wavelength; the photosensitizer includes a porphyrin or porphyrin derivative; the photosensitizer includes chlorin e6 or a chlorin derivative.

In preferred embodiments the conjugate further includes a backbone member. In such embodiments the backbone is coupled both to a photosensitizer and to a targeting moiety. The backbone can itself also be a targeting moiety, e.g. polylysine.

In preferred embodiments the conjugate includes chlorin e6 conjugated to polylysine, e.g., 1 or 2 to 20 chlorin e6 molecules conjugated to a polylysine between about 1,000 and 3,000 in molecular weight.

In preferred embodiments the conjugate includes chlorin e6 conjugated to a histatin polypeptide, or an active fragment or analog thereof, e.g., 1 or 2 to 4 chlorin e6 molecules conjugated to a histatin-5 polypeptide.

In preferred embodiments the conjugate includes chlorin e6 and a histatin polypeptide, or an active fragment or analog thereof, conjugated to a polylysine backbone, e.g., either from one to 4 polylysine chains (MW 1,000 to 3,000 daltons, each containing from 1 or 2 to 20 chlorin e6 molecules) joined to one histatin-5 polypeptide, or from one to 4 histatin-5 polypeptides joined to a polylysine chain (MW 1,000 to 3,000 and containing 1 or 2 to 16 chlorin e6 molecules.

In preferred embodiments the target organism is an oral bacterial species, e.g., *Porphyromonas* (*Bacteroides*) *gingivalis*.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

In preferred embodiments, the targeting moiety includes a salivary polypeptide, or an active fragment or analog thereof. Examples of salivary polypeptides are the histatins, e.g., histatin-1 through -8, or more preferably, histatin-1, -3, or -5. In preferred embodiments the targeting moiety includes histatin-5 residues 13–24, or corresponding residues from other histatins. In preferred embodiments the targeting moiety includes a histatin molecule which has been engineered to include an internal duplication.

In another aspect, the invention features, a method of treating a subject, for a disorder characterized by the presence of an unwanted organism. The method includes:
administering to the subject, a conjugate which includes a photosensitizer coupled to a NPM targeting moiety, e.g., a conjugate described herein;
irradiating the subject with energy of a wavelength appropriate to produce a cytotoxic effect by the photosensitizer;
thereby treating the subject, for the disorder characterized by the presence of an unwanted organism.

In preferred embodiments, the unwanted organism, by way of example, can be: a microorganism, e.g., a bacterial cell, a fungal cell, a protozoan cell, a cell of *Pneumocystis carinii*; a virus; or, a parasitic helminth; or an arthropod.

In preferred embodiments where the unwanted organism is a bacterial cell, the bacterial cell can be a Staphylococcus, Streptococcus, Enterococcus, Mycobacterium, Pseudomonas, Salmonella, Shigella, Escherichia, Erwinia, Klebsiella, Borrelia, Treponema, Campylobacter, Helicobacter, Bordetella, Neisseria, Legionella, Leptospira, Serpulina, Mycoplasma, Bacteroides, Klebsiella, Yersinia, Chlamydia, Vibrio, Actinobacillus, Porphyria, Hemophilus, Pasteurella, Peptostreptococcus, Listeria, Propionibacterium, Mycobacterium, Corynebacterium or Dermatophilus cell. In more preferred embodiments the bacterial cell can be a *Porphyromonas* (*Bacteroides*) *gingivalis*; Bacteroides species including *B. gingivalis* (now known as *Porphyromonas gingivalis*), *Eikenella corrodens*, *Fusobacterium nucleatum*, *Wolinella recta*, Eubacterium species, *Prevotella* (*Bacteroides*) *intermedia*, *Bacteroides forsythus*, Capnocytophaga species, *Actinobacillus actinomycetamcomitans*, and *Streptococcus mutans*.

In preferred embodiments where the bacterial cell is a Treponema cell, the disorder is trenchmouth, yaws, or pinta. In other embodiments the disorder is impetigo or cystic acne.

In preferred embodiments where the unwanted organism is a fungal cell, the cell can be a Candida or an Aspergillus cell. In preferred embodiments, the organism is *Pneumocystis carinii*.

In preferred embodiments where the unwanted organism is a protozoan cell, the cell is an Entamoeba, a Toxoplasma, a Giardia, a Leishmania, a Crytosporidium, or a Schistosoma.

In preferred embodiments where the unwanted organism is a virus, the virus is an HIV, an HTLV, a hepatitis virus, an influenza virus, a rhinovirus, a papilloma virus, a measles virus, a Herpes virus, a rotavirus, a parvovirus, a psittacosis virus, or an Ebola virus.

In preferred embodiments where the target organism is an arthropod, the arthropod is a parasitic mite.

In preferred embodiments where the target organism is a helminth, the helminth is a nematode or a trematode. In preferred embodiments where the helminth is a nematode, the nematode is found in a subject with filariasis.

In preferred embodiments the target organism is an oral bacterial species, e.g., *Porphyromonas* (*Bacteroides*) *gingivalis*.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

In another aspect, the invention features, a method of treating a subject, for a disorder of the oral cavity characterized by the presence of an unwanted organism. The method includes:
administering to the subject, a conjugate which includes a photosensitizer coupled to a NPM targeting moiety, e.g., a conjugate described herein;
irradiating the subject with energy of a wavelength appropriate to produce a cytotaxic effect by the photosensitizer;
thereby treating the subject, for the disorder characterized by the presence of an unwanted organism.

In preferred embodiments the method includes topically administering the conjugate to an area of the subject which is infected with the unwanted organisms. The conjugate can be topically administered e.g., generally to the surfaces of the oral cavity, to the gums, to the periodontal tissue, to the periodontal pocket, to areas characterized by inflammation, to lesions, to fissures or imperfections in a tooth or gum, to dental carries, to cuts or incisions, e.g., those made in the course of dental or other medical care, or to wounds. In other embodiments the method includes systemic administration, e.g., by ingestion or injection. In other embodiments the method includes subcutaneous delivery, e.g., subcutaneous injection. In other embodiments the method includes local injection at or near the site of infection with the unwanted organism.

In preferred embodiments the radiation: is laser irradiation; or is delivered with a fiber optic devise.

In preferred embodiments the subject is suffering from: a disorder of the oral cavity which is characterized by the presence of an unwanted organism, e.g., a microbial organism, e.g., an unwanted bacterium, fungus, virus, or protozoan. The disorder can be one in which any of the teeth, gums, e.g., the periodontal tissue, tongue, tonsils, uvula, lining of the oral cavity, or parotid glands, are infected by the organism or otherwise affected by the disorder.

In preferred embodiments the disorder is an infectious oral disease.

In preferred embodiments the subject is suffering from: a periodontal disease, e.g., periodontitis or periodontosis; receding gums; acute ulcerative gingivitis; chronic gingivitis; periodontal abscess; early onset (juvenile) periodontitis; gingivitis of pregnancy; pericoronitis; infective stomatitis; cancrum oris; suppurative paratitis; acute or chronic osteomyelitis of the mandibles or maxilla; pulpitis or periapical infections.

In preferred embodiments the subject is suffering from an oral fungal infection, e.g., an actinomycosis, histoplasmosis, phycomycosis, aspergillosis, cryptococcosis, sporotrichosis, blastomycosis, or paracoccidioidomycosis infection.

In other preferred embodiments, the subject is suffering from an oral yeast infection, e.g., including a Candida infection of the oral cavity, e.g., candidosis (candidiasis), thrush, chronic candidosis and candidal (candididal) leukoplakia, or from a viral infection including primary herpetic stomatitis, or herpes labialis.

In preferred embodiments the subject, in addition to suffering from a disorder of the oral cavity, is suffering from an immune disorder, e.g., an acquired or inherited immune disorder. In particularly preferred embodiments the subject is suffering from AIDS or is HIV positive.

In preferred embodiments the unwanted organism is: an oral bacterial species, e.g., *Porphyromonas* (*Bacteroides*) *gingivalis;* Bacteroides species including *B. gingivalis* (now known as *Porphyromonas gingivalis*), *Eikenella corrodens, Fusobacterium nucleatum, Wolinella recta,* Eubacterium species, *Prevotella* (*Bacteroides*) *intermedia, Bacteroides forsythus,* Capnocytophaga species, *Actinobacillus actinomycetamcomitans,* and *Streptococcus mutans.*

In preferred embodiments, the targeting moiety of the conjugate includes a salivary polypeptide, or an active fragment or analog thereof. Examples of salivary polypeptides are the histatins, e.g., histatin-1 through -8, or more preferably, histatin-1, -3, or -5. In preferred embodiments the targeting moiety includes histatin-5 residues 13–24, or corresponding residues from other histatins. In preferred embodiments the targeting moiety includes a histatin molecule which has been engineered to include an internal duplication.

In particularly preferred embodiments the targeting moiety includes a polylysine molecule.

In preferred embodiments the targeting moiety includes a polypeptide, e.g., a polyamino acid, which has been chemically modified to alter its charge, e.g., the charge of side chains of one or more amino acid residues of the polyamino acid. For example, one or more, or approximately 10, 25, 50, 75, 90 or 100% of the charged side chains can be modified. By modified is meant that a negative side chain, e.g., a glutamic acid, or an aspartic acid, side chain is made positive or neutral in charge, a positively charged side chain, e.g., the side chain of lysine, arginine, or ornithine is made negative or neutral in charge. By way of example, one or more of the side chains of polylysine can be made neutral or negative in charge.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

In preferred embodiments: the photosensitizer produces singlet oxygen upon absorption of electromagnetic irradiation at the proper energy level and wavelength; the photosensitizer includes a porphyrin or porphyrin derivative; the photosensitizer includes chlorin e6 or a chlorin derivative.

In another aspect, the invention features a method of treating a subject for a periodontal disorder characterized by the presence of an unwanted organism. The method includes:

administering to the subject, a conjugate which includes a photosensitizer coupled to a NPM targeting moiety, e.g., a conjugate described herein;

irradiating periodontal tissue of the subject with energy of a wavelength appropriate to produce a cytotaxic effect by the photosensitizer;

thereby treating the subject, for the periodontal disorder.

In preferred embodiments the method includes topically administering the conjugate to an area of the subject which is infected with the unwanted organisms. The conjugate can be topically administered to the gums, to the periodontal tissue, to the periodontal pocket, to areas characterized by inflammation, or lesions. In other embodiments the method includes systemic administration, e.g., by ingestion or injection. In other embodiments the method includes subcutaneous delivery, e.g., subcutaneous injection. In other embodiments the method includes local injection at or near the site of infection with the unwanted organism.

In preferred embodiments the subject is suffering from: periodontitis or periodontosis; receding gums; acute ulcerative gingivitis; chronic gingivitis; periodontal abscess; early onset (Juvenile) periodontitis; gingivitis of pregnancy.

In preferred embodiments the subject, in addition to suffering from a periodontal disorder, is suffering from an immune disorder, e.g., an acquired or inherited immune disorder. In particularly preferred embodiments the subject is suffering from AIDS or is HIV positive.

In preferred embodiments the unwanted organism is: an oral bacterial species, e.g., *Porphyromonas* (*Bacteroides*) *gingivalis;* Bacteroides species including *B. gingivalis* (now known as *Porphyromonas gingivalis*), *Eikenella corrodens, Fusobacterium nucleatum, Wolinella recta,* Eubacterium species, *Prevotella* (*Bacteroides*) *intermedia, Bacteroides forsythus,* Capnocytophaga species, *Actinobacillus actinomycetamcomitans,* and *Streptococcus mutans.*

In preferred embodiments, the targeting moiety of the conjugate includes a salivary polypeptide, or an active fragment or analog thereof. Examples of salivary polypeptides are the histatins, e.g., histatin-1 through -8, or more preferably, histatin-1, -3, or -5. In preferred embodiments the targeting moiety includes histatin-5 residues 13–24, or corresponding residues from other histatins. In preferred embodiments the targeting moiety includes a histatin molecule which has been engineered to include an internal duplication.

In particularly preferred embodiments the targeting moiety includes a polylysine molecule.

In preferred embodiments the targeting moiety includes a polypeptide, e.g., a polyamino acid, which has been chemically modified to alter its charge, e.g., the charge of side chains of one or more amino acid residues of the polyamino acid. For example, one or more, or approximately 10, 25, 50, 75, 90 or 100% of the charged side chains can be modified. By modified is meant that a negative side chain, e.g., a glutamic acid, or an aspartic acid, side chain is made positive or neutral in charge, a positively charged side chain, e.g., the side chain of lysine, arginine, or ornithine is made negative or neutral in charge. By way of example, one or more of the side chains of polylysine can be made neutral or negative in charge.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

In preferred embodiments: the photosensitizer produces singlet oxygen upon absorption of electromagnetic irradiation at the proper energy level and wavelength; the photosensitizer includes a porphyrin or porphyrin derivative; the photosensitizer includes chlorin e6 or a chlorin derivative.

In another aspect, the invention features, a method of treating a subject having an acquired immune disorder having an acquired immune disorder, for a disorder of the oral cavity characterized by the presence of an unwanted organism. In preferred embodiments the unwanted organism is other than an organism which is causative of the acquired immune disorder. The acquired immune disorder can be, e.g., AIDS, or an HIV infection. The method includes:

administering to the subject, a conjugate which includes a photosensitizer coupled to a NPM targeting moiety, e.g., a conjugate described herein;

irradiating the subject with energy of a wavelength appropriate to produce a cytotaxic effect by the photosensitizer;

thereby treating the subject, for the disorder characterized by the presence of an unwanted organism.

In preferred embodiments the method includes topically administering the conjugate to an area of the subject which is infected with the unwanted organisms. The conjugate can be topically administered e.g., generally to the surfaces of the oral cavity, to the gums, to the periodontal tissue, to the periodontal pocket, to areas characterized by inflammation, to lesions, to fissures or imperfections in a tooth or gum, to dental carries, to cuts or incisions, e.g., those made in the course of dental or other medical care, or to wounds. In other embodiments the method includes systemic administration, e.g., by ingestion or injection. In other embodiments the method includes subcutaneous delivery, e.g., subcutaneous injection. In other embodiments the method includes local injection at or near the site of infection with the unwanted organism.

In preferred embodiments the radiation: is laser irradiation; or is delivered with a fiber optic devise.

In preferred embodiments the unwanted organism is, e.g., a microbial organism, e.g., an unwanted bacterium, fungus, virus, or protozoan. The disorder can be one in which any of the teeth, gums, e.g., the periodontal tissue, tongue, tonsils, uvula, lining of the oral cavity, parotid glands, are infected by the organism or otherwise affected by the disorder.

In preferred embodiments the disorder is an infectious oral disease.

In preferred embodiments the subject is suffering from: a periodontal disease, e.g., periodontitis or periodontosis; receding gums; acute ulcerative gingivitis; chronic gingivitis; periodontal abscess; early onset juvenile) periodontitis; gingivitis of pregnancy; periocoronities; infective stomatitis; cancrum oris; suppurative paratitis; acute or chronic osteomyelitis of the mandibles or maxilla; pulpitis or perioapical infections.

In preferred embodiments the subject is suffering from an oral fungal infection, e.g., an actinomycosis, histoplasmosis, phycomycosis, aspergillosis, cryptococcosis, sporotrichosis, blastombycosis, or paracoccidioidomycosis infection. In other preferred embodiments, the subject is suffering from an oral yeast infection, e.g., including a Candida infection of the oral cavity, e.g., candidosis (candidiasis), thrush, chronic candidosis and candidal (candididal) leukoplakia, or from a viral infection including primary herpetic stomatitis, or herpes labialis.

In preferred embodiments the unwanted organism is: an oral bacterial species, e.g., *Porphyromonas* (*Bacteroides*) *gingivalis;* Bacteroides species including *B. gingivalis* (now known as *Porphyromonas gingivalis*), *Eikenella corrodens, Fusobacterium nucleatum, Wolinella recta,* Eubacterium species, *Prevotella* (*Bacteroides*) *intermedia, Bacteroides forsythus,* Capnocytophaga species, *Actinobacillus actinomycetamcomitans,* and *Streptococcus mutans.*

In preferred embodiments, the targeting moiety of the conjugate includes a salivary polypeptide, or an active fragment or analog thereof. Examples of salivary polypeptides are the histatins, e.g., histatin-1 through -8, or more preferably, histatin-1, -3, or -5. In preferred embodiments the targeting moiety includes histatin-5 residues 13–24, or corresponding residues from other histatins. In preferred embodiments the targeting moiety includes a histatin molecule which has been engineered to include an internal duplication.

In particularly preferred embodiments the targeting moiety includes a polylysine molecule.

In preferred embodiments the targeting moiety includes a polypeptide, e.g., a polyamino acid, which has been chemically modified to alter its charge, e.g., the charge of side chains of one or more amino acid residues of the polyamino acid. For example, one or more, or approximately 10, 25, 50, 75, 90 or 100% of the charged side chains can be modified. By modified is meant that a negative side chain, e.g., a glutamic acid, or an aspartic acid, side chain is made positive or neutral in charge, a positively charged side chain, e.g., the side chain of lysine, arginine, or ornithine is made negative or neutral in charge. By way of example, one or more of the side chains of polylysine can be made neutral or negative in charge.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

In preferred embodiments: the photosensitizer produces singlet oxygen upon absorption of electromagnetic irradiation at the proper energy level and wavelength; the photosensitizer includes a porphyrin or porphyrin derivative; the photosensitizer includes chlorin e6 or a chlorin derivative.

In another embodiment, the invention includes a method for making conjugate molecules, the method comprising:

supplying a backbone, e.g., a polypeptide backbone;

coupling, e.g., covalently coupling, a photosensitizer to the backbone;

coupling, e.g., covalently coupling, a targeting moiety, e.g., a targeting moiety described herein, to the backbone.

In preferred embodiments, the coupling reactions involve an activated ester moiety of a photosensitizer. In more preferred embodiments, an amino group on the backbone reacts as a nucleophile, displacing the leaving group from the photosensitizer active ester. In preferred embodiments, the targeting moiety is coupled to the backbone with a coupling agent.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

In another aspect, the invention features, a kit for elimination of an unwanted organism. The kit includes a photosensitizer coupled to a targeting moiety and instructions for use.

In preferred embodiments, the conjugate does not include, e.g., it is not coupled, e.g., covalently or non-covalently coupled to: a PM; an antibody; an enzyme; a hormone; a receptor on a cell surface; or the ligand for a receptor on a cell surface.

Photodynamic therapy involves the use of a light activatable compound, or photosensitizer, together with light of the correct wavelength, to produce a cytotoxic effect. In order to increase the specificity of the photosensitizer for its target, the photosensitizer may be bound to a targeting moiety. Methods and conjugates of the invention features the use of NPM-targeted photosensitizers. NPM's can deliver photosensitizer to a target in an efficient and cost effective manner. Compositions of the invention are advantageous in that (i) they do not need to be internalized to kill bacteria, since illumination generates toxic oxygen species which can diffuse through the bacterial cell wall, (ii) the generation of toxic oxygen species can have a local effect in stimulating the host immune response which can assist in eradicating bacteria and in promoting healing of the wound, (iii) they produce a cytotoxic response only in the area subject to illumination.

Unless otherwise defined, all technical and scientific terms used herein have the same meaning as commonly understood by one of ordinary skill in the art to which this invention belongs. Although methods and materials similar or equivalent to those herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

DETAILED DESCRIPTION OF THE INVENTION

Figure 1A:
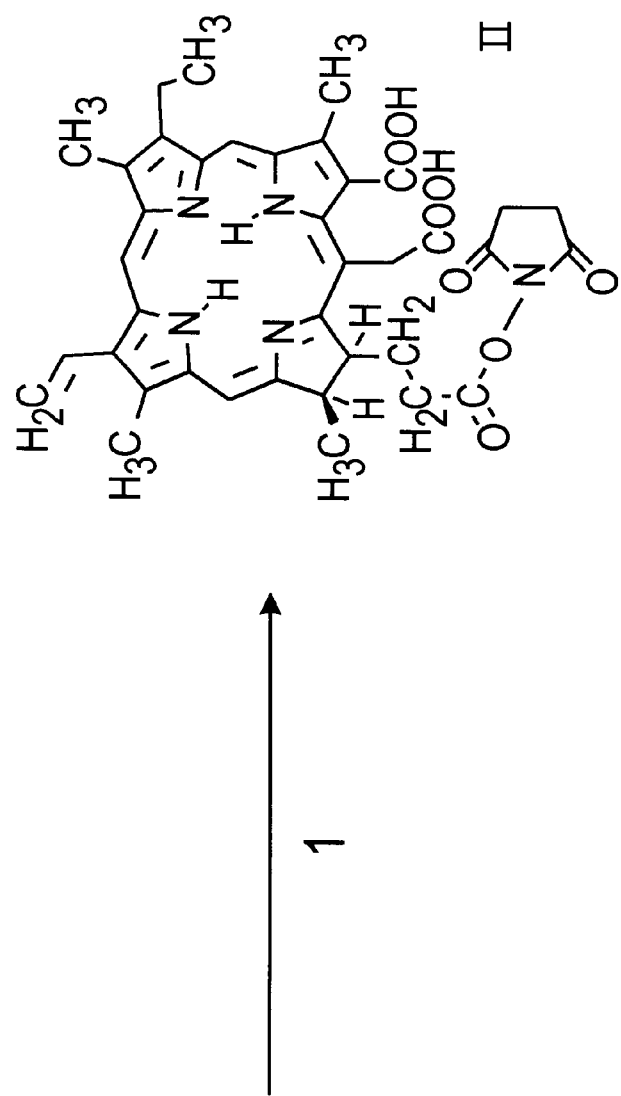
FIG. 1A is a diagram of the first of the reactions for synthesis of chlorin e6 polylysine conjugates of different charge, with arrow 1 showing the reaction of chlorin e6, molecule I, with N-hydroxysuccinimide in the presence of dicyclohexylcarbodiimide and dimethyl sulfoxide to form chlorin e6-NHS ester, molecule II.

As used herein, a photosensitizer refers to a substance which, upon irradiation with electromagnetic energy of the appropriate wavelength, usually light of the appropriate wavelength, produces a cytotoxic effect.

As used herein, the terms peptide, polypeptide, and protein are, unless specified otherwise, used interchangeably. Peptides, polypeptides, and proteins used in methods and compositions described herein can be recombinant, purified from natural sources, or chemically synthesized. For example, reference to the use of a bacterial protein or a protein from bacteria, includes the use of recombinantly produced molecules, molecules purified from natural sources, or chemically synthesized molecules.

As used herein, a non-pair-member (NPM) is a molecule, e.g., a polypeptide, which binds to a target site. A target site can be a protein, nucleic acid, lipid, polysaccharide, or a structure which is a combination thereof. Antibodies, receptors, hormones, growth factors, neurotransmitters and enzymes are not NPM polypeptides and are referred to herein as pair-members (PM's). NPM's do not exhibit a complementary relationship between the NPM and the binding site. By complementary relationship is meant that the two entities which bind, have a complementary combination of shape, contour, and charge which is based on the ability of "opposing" functional groups located on one entity being capable of forming non-covalent bonds with "opposing" functional groups located on the other entity, thereby complexing the two entities with a plurality of non-covalent interactions. In other words, the NPM will not contain a combination of shape, contours, and charge patterns that are complementary to those of the target site. Generally, a NPM will have lower affinity for its target than do PM's, e.g., the PM's described above. Typical affinities of NPM's for their targets are in the Km range values of mM to $\mu$M. Release of the binding of PM's, for example, an enzyme from a substrate, in vivo, often requires the binding of an additional protein, or the breaking or forming of a covalent bond. In vitro, PM pairs are often manipulated to separate into component entities by extremes of heat or pH.

Methods of the invention can use a targeting moiety which has a PM function in addition to the binding characteristic to be used for the purposes of the instant invention. For example, LDL molecules bind as PM-type ligands to apo B/E classical LDL receptors, and oxidized or otherwise altered LDL molecules bind as PM-type ligands to macrophage scavenge receptors. However, LDL molecules have, in addition, an NPM-type affinity for Gram negative surface components, which is not a PM function, as defined herein. PM interactions are generally characterized by high specificity, so that only one or a few cognate molecules are recognized, and high affinity, with Km values generally in the range of $\mu$M to pM.

As used herein, target organism, means an organism which causes or aggravates a disorder.

The term "subject," as used herein, refers to a living animal or human carrying an unwanted organism, that is, an organism that is a target for photodynamic therapy. The subject may be immune deficient. The subject can be a mammal, including humans and non-human mammals such as dogs, cats, pigs, cows, sheep, goats, horses, rats, and mice. The subject may formerly have been treated by chemotherapy or antibiotic therapy.

As used herein, "naturally occurring" refers to a molecule which exists in nature. A non-naturally occurring molecule is one having a structure which does not occur without human intervention.

As used herein, the term small anti-microbial peptide (SAMP) refers to a peptide of less than 60 amino acid residues in length. Histatins, defensins, cecropins, magainins, Gram positive bacteriocins, and peptide antibiotics which meet this limitation are SAMP's. Many SAMP's are in the range of 20–40 amino acid residues in length. SAMP's are naturally occurring peptides, and are made by a wide variety of organisms. SAMP's are NPM's. Many SAMP's have a broad spectrum of antimicrobial activity, and, e.g., can kill more than one species, and in some cases can kill distantly related species, e.g. Gram negative and Gram positive bacterial species.

As used herein, an active fragment or analog of a polypeptide is one which retains at least 20% of the antimicrobial activity or target organism affinity of the polypeptide. Analogs of a polypeptide share at least 50% and more preferably 60, 70, 80 or 90% sequence identity with the polypeptide.

A salivary polypeptide, as used herein, refers to a polypeptide produced by a subject and found in the subject's saliva. Most salivary polypeptides are produced by the parotid gland.

As used herein, a peptide antibiotic is a linear or cyclic oligopeptide, or an active fragment, or analog thereof, which possesses antibiotic activity against bacterial or fungal species, and which is synthesized enzymatically on a multiprotein complex to which it is attached by a thioether bond. A peptide antibiotic may include non-ribosomal amino acids such as D amino acids, and may include non-amino acid residues such as esters of lactic acid or valeric acid.

Photosensitizers

A photosensitizer is a substance which, upon irradiation with electromagnetic energy of the appropriate wavelength, usually light of the appropriate wavelength, produces a cytotoxic effect.

Many photosensitizers produce singlet oxygen. Upon electromagnetic irradiation at the proper energy level and wavelength, such a photosensitizer molecule is converted to an energized form. The energized form can react with atmospheric $O_2$, such that upon decay of the photosensitizer to the unenergized state, singlet oxygen is produced. Singlet oxygen is highly reactive, and is toxic to a proximal target organism.

The life-time of its triplet energized state should be of sufficient duration (e.g., several microseconds) to permit interaction with neighboring molecules to produce cytotoxic species.

A photosensitizer composition should efficiently absorb electromagnetic energy of the appropriate wavelength with high quantum yield to efficiently generate the energized form of the photosensitizer. Toxicity to the target organism should increase substantially, preferably 10-fold, 100-fold, or even more preferably 1,000-fold, upon irradiation. A photosensitizer should exhibit low background toxicity, i.e., low toxicity in the absence of irradiation with energy of the appropriate wavelength.

Other preferred properties of a photosensitizer include high solubility and stability in appropriate solvents. For example, a photosensitizer should be soluble under conditions used to couple it to the targeting moiety or backbone. Desired solubility properties will differ with the conditions chosen for the reaction but solubility in DMSO, water, ethanol, or a mixture of water and DMSO or in ethanol, such as DMSO: $H_2O$, or in ethanol:water 5%, 10% or 15% can be useful. Solubility is preferably 50 µg/ml, 100 µg/ml, 500 µg/ml, 1 mg/ml or 10 mg/ml in an aqueous solvent or ethanol:water solvent.

When conjugated to a targeting moiety, the resulting photosensitizer:targeting moiety conjugate should be soluble under physiological conditions, in aqueous solvents containing appropriate carriers and excipients, or other delivery systems such as in liposomes. The molecules of the invention may be delivered as free photosensitizer:targeting moiety compositions in solution, and may be delivered also in various formulations including, but not limited to, liposome, peptide/polymer-bound, or detergent-containing formulations.

The compositions of the invention should be stable during the course of at least a single round of treatment by continuous or pulsed irradiation, during which each molecule of the composition would preferably be repeatedly excited to the energized state, undergoing multiple rounds of generation of singlet oxygen. Preferable stability of a photosensitizer conjugate molecule is survival of 10%, 50%, 90%, 95%, or 99% of molecules in active form for 1 hour, for 30 min, 15 min or for at least 1 min at 37° C., under physiological conditions.

Photosensitizers include, but are not limited to, hematoporphyrins, such as hematoporphyrin HCl and hematoporphyrin esters (Dobson, J. and M. Wilson, *Archs. Oral Biol.* 37:883–887); dihematophorphyrin ester (Wilson, M. et al., 1993, *Oral Microbiol. Immunol.* 8:182–187); hematoporphyrin IX (Russell et al., 1991, *Can J. App. Spectros.* 36:103–107, available from Porphyrin Products, Logan, Utah) and its derivatives; 3,1-meso tetrakis(o-propionamidophenyl)porphryrin; hydroporphyrins such as chlorin, herein, and bacteriochlorin of the tetra (hydroxyphenyl)porphyrin series, and synthetic diporphyrins and dichlorins; o-substituted tetraphenyl porphyrins (picket fence porphyrins); chlorin e6 monoethylendiamine monamide (CMA Goff, B. A. et al., 1994, 70:474–480, available from Porphyrin Products, Logan, Utah); mono-1-aspartyl derivative of chlorin e6, and mono- and di-aspartyl derivatives of chlorin e6; the hematoporphyrin mixture Photofrin II (Quardra Logic Technologies, Inc., Vancouver, BC, Canada); benzophorphyrin derivatives (BPD), including benzoporphyrin monoacid Ring A (BPD-MA), tetracyanoethylene adducts, dimethyl acetylene dicarboxylate adducts, Diels-Adler adducts, and monoacid ring "a" derivatives; a naphthalocyanine (Biolo, R., 1994, *Photochem. and Photobiol.* 5959:362–365); a Zn(II)-phthalocyanine (Shopora, M. et al., 1995, *Lasers in Medical Science* 10:43–46); toluidine blue O (Wilson, M. et al., 1993, *Lasers in Medical Sci.* 8:69–73); aluminum sulfonated and disulfonated phthalocyanine ibid.; and phthalocyanines without metal substituents, and with varying other substituents; a tetrasulfated derivative; sulfonated aluminum naphthalocyanines; methylene blue (ibid.); nile blue; crystal violet; azure β chloride; and rose bengal (Wilson, M., 1994, *Intl. Dent. J.* 44:187–189). Numerous photosensitizer entities are disclosed in Wilson, M. et al., 1992, *Curr. Micro.* 25:77–81, and in Okamoto, H. et al., 1992, *Lasers in Surg. Med.* 12:450–485.

Other potential photosensitizer compositions include but are not limited to, pheophorbides such as pyropheophorbide compounds, anthracenediones; anthrapyrazoles; aminoanthraquinone; phenoxazine dyes; phenothiazine derivatives; chalcogenapyrylium dyes including cationic selena- and tellura-pyrylium derivatives; verdins; purpurins including tin and zinc derivatives of octaethylpurpurin and etiopurpurin; benzonaphthoporphyrazines; cationic imminium salts; and tetracyclines.

The suitability of a photosensitizer for use in a conjugate can be determined by methods described herein or by methods known to those skilled in the art.

The efficiency with which a photosensitizer oxidizes a target molecule is a measure of the usefulness. The efficiency of the oxidation of a target molecule by a photosensitizer can be determined in vitro. Examples of substrates include 4-nitroso-N,N-dimethylaniline (RNO; Hasan, T. et al., 1987, *Proc. AACR* 28:395 Abstr. 1,568), and tryptophan or histidine (Lambert, C. R. et al., 1986, *Photochem. Photobiol.* 44:595–601). In these assays, ability of a candidate photosensitizer to "bleach" the substrate can be monitored spectroscopically. The advantage of a chemical assay is that a large number of putative photosensitizer compositions can be simultaneously screened. Parameters which can be varied include photosensitizer concentration, substrate concentration, optimal intensity of irradiation, and optimal wavelength of irradiation. High through-put technologies including plastic multi-well dishes, automated multi-pipetters, and on-line spectrophotometric plate readers can be used. Undesirable candidates, e.g., compositions having high backgrounds under unirradiated conditions, inefficient energy capture or reactive potential, can be identified and eliminated.

In vivo assays with cells of one or more model target organisms can be used to evaluate a photosensitizer for cytotoxicity of its background and activated forms. The efficiency of killing of the organism in the presence of the irradiated and unirradiated photosensitizer can be measured and compared to survival of the untreated control cell sample. This assay can be automated. The use of counts of colony forming units (CFU) or cell growth may require incubation of the samples that have been applied to a nutrient medium, with a concomitant lag of the appropriate growth period to allow for colony formation.

Survival of cells of the model target organism can alternatively be monitored by assay of a biochemical process, for example, assay of DNA synthesis. In this approach the effectiveness of a photosensitizer candidate can be measured by its effect on samples of cells of the model organism, which are also exposed to a labeled DNA precursor such as tritiated thymidine. Cells are then collected, washed to remove unincorporated precursor, and monitored for uptake of the precursor and incorporation into acid-insoluble precipitate, which is a measure of quantity of DNA synthesis. In this assay, which can also be automated as described above, quantitative evaluation of the effects of presence of irradiated photosensitizer compositions can be readily evaluated and quantitated. In control unirradiated cells and in untreated cells, DNA synthesis increases logarithmically as a function of cell growth. A positive result indicating presence of a putative successful novel photosensitizer, is turn-off of DNA synthesis in cells that have been irradiated in the presence of that photosensitizer.

Suitable model target organisms are: *Escherichia coli, Pseudomonas aeruginosa, Staphylococcus aureus* and *Streptococcus mutans*. A suitable positive control for photosensitizer activity is toluidine blue O.

If large numbers of candidates are to be screened it may be desirable to use a two-stage screen, wherein the first stage is an in vitro screen and wherein the second stage uses cells.

Irradiation

Irradiation of the appropriate wavelength for a given compound may be administered by a variety of methods.

These methods include but are not limited to the administration of laser, nonlaser, or broad band light. Irradiation can be produced by extracorporeal or intraarticular generation of light of the appropriate wavelength. Light used in the invention may be administered using any device capable of delivering the requisite power of light including, but not limited to, fiber optic instruments, arthroscopic instruments, or instruments which provide transillumination. Delivery of light to the oral cavity can be accomplished with flexible fiber optics which are inserted into the periodontal pocket, or by transgingival illumination (average thickness of gingiva is 5–7 mm). The source of the light needed to inactivate the bacteria can be an inexpensive diode laser or a non-coherent light source.

Coupling Technologies

The term "coupling agent" as used herein, refers to a reagent capable of coupling a photosensitizer to a targeting moiety, or a photosensitizer or a targeting moiety to a "backbone" or "bridge" moiety. Any bond which is capable of linking the components such that they are stable under physiological conditions for the time needed for administration and treatment is suitable, but covalent linkages are preferred. The link between two components may be direct, e.g., where a photosensitizer is linked directly to a targeting moiety, or indirect, e.g., where a photosensitizer is linked to an intermediate, e.g., linked to a backbone, and that intermediate being linked to the targeting moiety. A coupling agent should function under conditions of temperature, pH, salt, solvent system, and other reactants that substantially retain the chemical stability of the photosensitizer, the backbone (if present), and the targeting moiety.

A coupling agent can link components without the addition to the linked components of elements of the coupling agent. Other coupling agents result in the addition of elements of the coupling agent to the linked components. For example, coupling agents can be cross-linking agents that are homo- or hetero-bifunctional, and wherein one or more atomic components of the agent can be retained in the composition. A coupling agent that is not a cross-linking agent can be removed entirely during the coupling reaction, so that the molecular product can be composed entirely of the photosensitizer, the targeting moiety, and a backbone moiety (if present).

Many coupling agents react with an amine and a carboxylate, to form an amide, or an alcohol and a carboxylate to form an ester. Coupling agents are known in the art, see, e.g., M. Bodansky, "Principles of Peptide Synthesis", 2nd ed., referenced herein, and T. Greene and P. Wuts, "Protective Groups in Organic Synthesis," 2nd Ed, 1991, John Wiley, NY. Coupling agents should link component moieties stably, but such that there is only minimal or no denaturation or deactivation of the photosensitizer or the targeting moiety.

The photosensitizer conjugates of the invention can be prepared by coupling the photosensitizer to targeting moieties using methods described in the following Examples, or by methods known in the art. A variety of coupling agents, including cross-linking agents, can be used for covalent conjugation. Examples of cross-linking agents include N,N'-dicyclohexylcarbodiimide (DCC; Pierce), N-succinimidyl-S-acetyl-thioacetate (SATA), N-succinimidyl-3-(2-pyridyldithio)propionate (SPDP), ortho-phenylenedimaleimide (o-PDM), and sulfosuccinimidyl 4-(N-maleimidomethyl)cyclohexane-1-carboxylate (sulfo-SMCC). See, e.g., Karpovsky et al. *J. Exp. Med.* 160:1686, 1984; and Liu, MA et al., *Proc. Natl. Acad. Sci. USA* 82:8648, 1985. Other methods include those described by Paulus, *Behring Ins. Mitt.*, No. 78, 118–132, 1985; Brennan et al. *Science* 229:81–83, 1985, and Glennie et al., *J. Immunol.*, 139: 2367–2375, 1987. A large number of coupling agents for peptides and proteins, along with buffers, solvents, and methods of use, are described in the Pierce Chemical Co. catalog, pages T-155-T-200, 1994 (3747 N. Meridian Rd., Rockford Ill., 61105, U.S.A.; Pierce Europe B.V., P.O. Box 1512, 3260 BA Oud Beijerland, The Netherlands), which catalog is hereby incorporated by reference.

DCC is a useful coupling agent (Pierce #20320; Rockland, Ill.). It promotes coupling of the alcohol NHS to chlorin e6 in DMSO (Pierce #20684), forming an activated ester which can be cross-linked to polylysine. DCC (N,N'-dicyclohexylcarbodiimide) is a carboxy-reactive cross-linker commonly used as a coupling agent in peptide synthesis, and has a molecular weight of 206.32. Another useful cross-linking agent is SPDP (Pierce #21557), a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting moiety. Other useful conjugating agents are SATA (Pierce #26102) for introduction of blocked SH groups for two-step cross-linking, which is deblocked with hydroxylamine-HCl (Pierce #26103), and sulfo-SMCC (Pierce #22322), reactive towards amines and sulfhydryls. Other cross-linking and coupling agents are also available from Pierce Chemical Co. (Rockford, Ill.); Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups can be joined to lysine $\epsilon$-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B., et al. *Ciba Found Symp.* 186:5–20, 1994.

The production and purification of photosensitizer:targeting moiety conjugates can be practiced by methods known in the art. Yield from coupling reactions can be assessed by spectroscopy of product eluting from a chromatographic fractionation in the final step of purification. The presence of uncoupled photosensitizer and reaction products containing the photosensitizer can be followed by the physical property that the photosensitizer moiety absorbs light at a characteristic wavelength and extinction coefficient, so incorporation into products can be monitored by absorbance at that wavelength or a similar wavelength. Coupling of one or more photosensitizer molecules to a targeting moiety or to a backbone shifts the peak of absorbance in the elution profile in fractions eluted using sizing gel chromatography, e.g., with the appropriate choice of Sephadex G50, G100, or G200 or other such matrices (Pharmacia-Biotech, Piscataway N.J.). Choice of appropriate sizing gel, for example Sephadex gel, can be determined by that gel in which the photosensitizer elutes in a fraction beyond the excluded volume of material too large to interact with the bead, i.e., the uncoupled starting photosensitizer composition interacts to some extent with the fractionation bead and is concomitantly retarded to some extent. The correct useful gel can be predicted be predicted from the molecular weight of the uncoupled photosensitizer. The successful reaction products of photosensitizer compositions coupled to additional moieties generally have characteristic higher molecular weights, causing them to interact with the chromatographic bead to a lesser extent, and thus appear in fractions eluting earlier than fractions containing the uncoupled photosensitizer substrate. Unreacted photosensitizer substrate generally appears in fractions characteristic of the starting material, and the yield from each reaction can thus be assessed both from size of the peak of larger molecular weight material, and the decrease in the peak of characteristic starting material. The area under the peak of the product fractions is converted to the size of the yield using the molar extinction coefficient.

The product can be analyzed using NMR, integrating areas of appropriate product peaks, to determine relative yields with different coupling agents. A red shift in absorption of a photosensitizer of several nm has often been observed following coupling to a polyamino acid. Coupling to a larger moiety such as a protein might produces a comparable shift, as coupling to an antibody resulted in a shift of about 3–5 nm in that direction compared to absorption of the free photosensitizer. Relevant absorption maxima and extinction coefficients in 0.1M NaOH/1% SDS are, for chlorin e6, 400 nm and 150,000 $M^{-1}$, $cm^{-1}$, and for benzoporphyrin derivative, 430 nm and 61,000 $M^{-1}$, $cm^{-1}$.

Backbone Moieties

Photosensitizer:targeting moiety conjugates of the invention include those in which a photosensitizer is coupled directly to a targeting moiety, such as a histatin. Other photosensitizer:targeting moiety conjugates of the invention include a "backbone" or "bridge" moiety, such as a polyamino acid, which backbone is coupled both to a photosensitizer and to a targeting moiety. The backbone can itself be a targeting moiety, e.g. polylysine (see Example 4 and FIGS. 5 and 6).

Inclusion of a backbone in a conjugate with a photosensitizer moiety and a targeting moiety can provide a number of advantages, including the provision of greater stoichiometric ranges of photosensitizer and targeting moieties coupled per backbone. If the backbone possesses intrinsic affinity for a target organism, the affinity of the composition can be enhanced by coupling to the backbone. The specific range of organisms that can be targeted with one composition can be expanded by coupling two or more different targeting moieties to a single photosensitizer-backbone composition.

Peptides useful in the methods and compounds of the invention for design and characterization of backbone moieties include poly-amino acids which can be homo- and hetero-polymers of L-, D-, racemic DL- or mixed L- and D-amino acid composition, and which can be of defined or random mixed composition and sequence. Examples of naturally-occurring peptides with mixed D and L amino acid residues include bacitracin and tyrocidin. These peptides may be modeled after particular natural peptides, and optimized by the technique of phage display and selection for enhanced binding to a chosen target, so that the selected peptide of highest affinity is characterized and then produced synthetically. Further modifications of functional groups can be introduced for purposes, for example, of increased solubility, decreased aggregation, and altered extent of hydrophobicity. Examples of nonpeptide backbones include nucleic acids and derivatives of nucleic acids such as DNA, RNA and peptide nucleic acids; polysaccharides and derivatives such as starch, pectin, chitins, celluloses and hemimethylated celluloses; lipids such as triglyceride derivatives and cerebrosides; synthetic polymers such as polyethylene glycols (PEGs) and PEG star polymers; dextran derivatives, polyvinyl alcohols, N-(2-hydroxypropyl)-methacrylamide copolymers, poly (DL-glycolic acid-lactic acid); and compositions containing elements of any of these classes of compounds.

Modification of the Charge of Conjugates

The affinity of a conjugate for a target organism can be refined by modifying the charge of a component of the conjugate.

Conjugates such as poly-L-lysine chlorin e6 can be made in varying sizes and charges (cationic, neutral, and anionic), for example, free $NH_2$ groups of the polylysine are capped with acetyl, succinyl, or other R groups to alter the charge of the final composition. Net charge of a conjugate of the present invention can be determined by isoelectric focusing (IEF). This technique uses applied voltage to generate a pH gradient in a non-sieving acrylamide or agarose gel by the use of a system of ampholytes (synthetic buffering components). When charged polypeptides are applied to the gel they will migrate either to higher pH or to lower pH regions of the gel according to the position at which they become non-charged and hence unable to move further. This position can be determined by reference to the positions of a series of known IEF marker proteins.

Due to the combination of polar charged groups on the polyaminoacid, and the hydrophobic attraction between the planar aromatic tetrapyrrole rings, these conjugates can adopt pH dependent conformations which can interact with bacterial cell walls. In addition, histatins and related polypeptides contain at least one lysine residue which by the application of two heterobifunctional reagents will lead to a covalent disulfide link between the histatin and the polylysine chlorin e6 molecules. The optimum composition, concentration and time of application of the photosensitizer to various pathogenic oral bacteria can be determined.

Targeting Moieties

Desirable characteristics for the targeting moieties include: specificity for one or more unwanted target organisms, affinity and avidity for such organisms, and stability with respect to conditions of coupling reactions and the physiology of the organ or tissue of use. Specificity need not be narrowly defined, e.g., it may be desirable for a targeting molecule to have affinity for a broad range of target organisms, such as all Gram negative bacteria.

The targeting moiety, when incorporated into a conjugate molecule of the invention, should be nontoxic to the cells of the subject.

Targeting moieties can be selected from the sequences of naturally occurring proteins and peptides, from variants of these peptides, and from biologically or chemically synthesized peptides. Naturally occurring peptides which have affinity for one or more target organism can provide sequences from which additional peptides with desired properties, e.g., increased affinity or specificity, can be synthesized individually or as members of a library of related peptides. Such peptides can be selected on the basis of affinity for the target organism.

Naturally occurring peptides with affinity for target organisms useful in methods and compounds of the invention, include salivary proteins, e.g., histatins, microbially-elaborated proteins, e.g., bacteriocins, peptides that bind and/or kill species that are closely related to the producing strains; and proteins produced by animal species such as defensins, which are produced by mammals, and the cecropins and magainins, produced by moths and amphibia, respectively.

Histatins, defensins, cecropins and magainins are examples of a class of polypeptides found widely in nature, which share the characteristics of small size (generally approximately 30 amino acid residues, and between 10 residues and 50 residues), broad specificity of anti-microbial activity, and low affinity for target organisms.

The use of histatins as a photosensitizer targeting moieties will allow targeting a photosensitizer to a bacterial cell while leaving the host tissue unharmed. Histatins are a family of histidine-rich cationic polypeptides which have bactericidal and candidacidal properties and are constituents of normal human saliva (Oppenheim, G. G. et al., *J. Biol. chem.* 263:7472–747, 1988). Their mechanism of action is thought to involve a combination of alpha-helical conformation and cationic charge leading them to insert between the polar head groups in the bacterial cell wall (Raj, P. A. et al., *J. Biol. Chem.* 269:9610–9619, 1994).

While histatins can be used usefully employed as oral bacteriocides, their action occurs over time periods of hours, leading to the problem of formulating delivery vehicles such as gels to keep the histatins in the region of infection. Photodynamic inactivation of oral bacteria, however, can require only brief application of the bacteria-targeted photosensitizer, such as by supplying in a mouthwash. Because bacteria are 50–100 times smaller than the average mammalian cell and the mechanism of photodynamic therapy is thought to involve the production of molecular species such as singlet oxygen which have very short diffusion distances in tissues (less than 50 nm for singlet oxygen), it can be seen that modest levels of sensitizer selectivity for bacteria may lead to high levels of selectivity in cytotoxicity. Low levels of PDT in humans and experimental animals have been shown to activate components of the host immune system such as macrophages and lymphocytes, and these activated host cells may play a part in destroying bacteria and helping the regeneration of tissue destroyed by disease.

Histatins-1, -3 and -5 each contain 7 residues of histidine, in a total polypeptide length of 38, 32 and 24 residues, respectively. Histatins have a number of activities, for example, an anti-fungal activity, for example, against Candida pathogens. (U.S. Pat. No. 5,486,503). Recombinant duplication of histatin-5 residues 13–24 gives a peptide with enhanced candidacidal activity (Zuo, F. et al., *Gene* 161:87–91, 1995). Histatin-5 is an inhibitor of the trypsin-like protease produced by the oral bacterial species *Porphyromonas* (*Bacteroides*) *gingivalis,* which protease is associated with tissue destruction of periodontal disease (Nishikata, M. et al., *Biochem. Biophys. Res. Comm.* 174:625–630, 1991). About 3,600 histatin-5 molecules bind *P. gingivalis* with a $K_d$ on the order of $10^{-6}$ M (Murakami, Y. et al., *FEMS Microbiol. Letts.* 82:253–256,1991). Histatins-5 and -8 inhibit coaggregation of *P. gingivalis* and *S. mitis* (Murakami, Y. et al., *Inf. Immun.* 59:3284–3286, 1991), which may modulate the attachment of *P. gingivalis* to Gram positive bacteria previously bound to oral tissues.

Histatin-5 has bactericidal activity against at least the oral bacterial species *P. gingivalis* (Colon, J. O. et al., *J. Dent. Res.* 72 IADR Abstr.:322, Abstr. 1751) and *Actinomyces viscosus, A. naeslundii,* and *A. odontolyticus* (Kalpidis, C. D. et al., op. cit. 71:305, Abstr. 1595). The direct anti-microbial activity against the latter species appears to be without receptor activity for agglutination of Actinomyces cells. A synthetic peptide of histatin-5 is a potent inhibitor of *P.* (*B.*) *gingivalis* hemagglutinin (Murakami, Y. et al., *Archs. Oral. Biol.* 35:775–777). The synthetic peptide is strongly cationic (containing 6 His, 4 Lys, and 3 Arg in 22 residues) and may function as the binding domain for *P. gingivalis* on epithelial cells, salivary pellicle, and Gram positive cells.

Histatins that have been chemically capped at the C- or N-terminus, and complexed with a metal, for example Ag, Cu, Zn or Sn, are suitable for a range of anti-microbial applications, such as antiplaque, anti-caries, anti-bad breath oral applications, deodorant applications, personal hygiene applications and so on (EPO Patent Application 721 774 A2).

Bacteriocins, which are proteins produced by bacteria and which kill other strains and species of bacteria (Jack, R. W. et al., *Microbiol. Rev.* 59:171–200, 1995) can be used as targeting moieties. An exemplary Gram positive bacteriocin is nisin, produced by *Lactococcus lactis* and accorded GRAS status (generally regarded as safe) by the Food and Drug Administration for application to food preservation.

The bacteriocins nisin, subtilin, epidermin, gallidermin, salivarin, and lacticin exemplify the "lantibiotic" class of Gram positive bacteriocin, which is defined as a bacteriocin in which one or more cysteine residues are linked to a dehydrated serine or threonine to form a thioether-linked residue known as lanthionine (Lan) or threo-β-methyllanthionine (MeLan). These are post-translational modifications found in these anti-microbial peptides by the producing cell. Lantibiotics contain leader peptide sequences of 18–24 residues, which are cleaved to yield an active antimicrobial peptide of about 22–35 residues. Growth of the producing bacterial species, and preparation and purification of bacteriocins are performed by published procedures and techniques which can be carried out by one of skill in the art. For example, Yang, R. et al., *Appl. and Env. Microbiol* 58: 3355–3359, 1992, describe purification of bacteriocins from each of 4 genera of lactic acid bacteria, by optimizing absorption onto the producing cells, followed by use of low pH for selective elution of greatly enriched bacteriocin fractions. Mutant forms of each of the bacteriocins nisin, produced by *Lactococcus lactis,* and of subtilin, produced by *Bacillus subtilis* have more desirable properties than the parental wild-type forms (Liu, W. and N. Hansen, *J. Biol. Chem.* 267:25,078–25,085, 1992). Procedures for isolation of appropriate genes and for mutagenesis and selection of strains carrying desirable mutations are found in Maniatis, T. et al, 1982, Molecular Cloning: a Laboratory Manual, Cold Spring Harbor Press, Cold Spring Harbor, N.Y., and in the subsequent second edition, Sambrook, J. et al., 1989.

Anti-microbial peptides are produced by a variety of animals (see review by Saberwal, G. and R. Nagaraj, *Biochim. Biophys. Act.* 1197:109–131, 1994). An example is a peptide of the cecropin family produced by Cecropia moths. Several cecropins contain 37 residues, of which 6 are lysine. Cecropins are active against both Gram positive and Gram negative bacteria. Other insect produced peptides include apidaecin (from honeybees), andropin (from fruit flies), and cecropin family members from bumble bees, fruit flies, and other insects.

The defensins are produced by mammals, including humans, and are generally about 29–34 residues in length, and the magainins (about 23 residues) are produced by amphibia such as *Xenopus laevis*. Defensins from human (HNP-1,-2,-3 and 4), guinea pig (GPNP), rabbit (NP-1, -2, -3A, -3B, -4 and -5) and rat (NP-1, -2, -3 and -4) share a significant number of regions of homology. Defensins can have antimicrobial activity against Gram positive bacteria or Gram negative bacteria and fungi, with minimal inhibitory concentrations in the mM range. Rabbit NP-1 and NP-2 are more potent antibacterial agents than others in this family. Other mammalian anti-microbial peptides include murine cryptdin, bovine granulocyte bactenecin and indolicidin, and seminal-plasmin from bovine semen. Additional amphibian anti-microbials include PGLA, XPF, LPF, CPG, PGQ, bombinin from *Bombina variegata*, the bombinin-like peptides BLP-1, -2, -3 and -4 from *B. orientalis,* and brevinins from *Rana esculenta.* Invertebrates such as the horseshoe crab can be a source of anti-microbial peptides such as the tachyplesins (I, II and III) and the polyphemusins (I and II).

Peptides in these families of antimicrobial agents are generally cationic, and can have a broad antimicrobial spectrum, including both antibacterial and antifungal activities. The addition of positively charged residues can enhance antimicrobial specific activity several fold. The positive charges are thought to assist in the insertion of the peptides into the membranes of the susceptible organisms, in which context the peptide molecules can form pores and cause efflux of ions and other metabolites. Structural studies of the Moses sole fish neurotoxin 33 residue peptide pardaxin, for example, reveals that succinylated pardaxin inserts into erythrocyte and model membranes more slowly than unmodified pardaxin. (Shai, Y et al., *J. Biol. Chem.* 265: 20, 202–20, 209, 1990). The positively charged magainin molecule can disrupt both the metabolism of *E. coli* and the electric potential of the mitochondrion (Westerhoff, H. V., et al., *Proc. Natl. Acad. Sci.* 86:6597–6601, 1989).

Novel peptides, for example a cecropin-melittin hybrid, and synthetic Denantiomers, have antimicrobial activity (Merrifield, R. B. et al., "Antimicrobial peptides," Ciba Foundation Symp. 186, John Wiley, Chichester, pp. 5–26, 1994). One such synthetic cecropin-melittin peptide is 5-fold more active against *Mycobacterium smegmatis* than rifampin.

Targeting moieties can be plant proteins with affinities for particular target organisms, for example, a member of the lectin protein family with affinity for polysaccharides.

Targeting moieties can be synthetic peptides, such as polylysine, polyarginine, polyornithine, and synthetic heteropolypeptides that comprise substantial proportions of such positively charged amino acid residues. Such peptides can be chemically synthesized or produced biologically in recombinant organisms, in which case the targeting moiety peptide can be produced as part of a larger protein, for example as the N-terminus residues, and cleaved from that larger protein. Polypeptides suitable as "backbone" and "bridge" moieties are also suitable as target moieties, if they have sufficient affinity for the target organism. Considerations described are thus appropriate to consideration of a targeting moieties. Targeting moieties can be synthesized and selected or enriched by the variety of methods described herein.

Targeting moieties need not be limited to peptide compositions, but can be lectins, polysaccharides, steroids, and metalloorganic compositions. Targeting moieties can be comprised of compositions that are composed both of amino acids and sugars, such as mucopolysaccharides. A useful targeting moiety can be partially lipid and partially peptide in nature, such as low density lipoprotein. Serum lipoproteins especially high density and low density lipoproteins (HDL and LDL) can bind to bacterial surface proteins (Emancipator, K. et al., Infect. Immun. 60:596–601, 1992). HDL and especially reconstituted HDL neutralizes bacterial lipopolysaccharide both in vitro and in vivo (Wurfel MM et al., J. Exp. Med. 181:1743—1754, 1995). Endogenous LDL can protect against the lethal effects of endotoxin and Gram negative infection (Netea, M., et al., J. Clin. Invest. 97:1366–1372, 1996). The appropriate binding features of the lipoproteins to bacterial surface components can be identified by methods of molecular biology known in the art, and the binding feature of lipoproteins can be used as the targeting moiety in photosensitizer compositions of the present invention.

Production and Screening of Peptide Targeting Moiety Candidates

The inventor has discovered that molecules, e.g., peptides, other than antibodies and members of a high affinity ligand pairs, can be used to target a photosensitizer to a target organism. The following methods can be used to modify or refine the targeting moieties disclosed herein or to discover new targeting moieties.

Once an example of a targeting moiety of reasonable affinity has been provided, one skilled in the art can alter the disclosed structure (of a polylysine polypeptide, for example), by producing fragments or analogs, and testing the newly produced structures for modification of affinity or specificity. Examples of methods which allow the production and testing of fragments and analogs are discussed below. These methods can be used to make fragments and analogs of a known naturally occurring polypeptide or protein which is a targeting moiety, e.g., a polypeptide such as histatin or low density lipoprotein, each of which has binding affinity for cells of one or more bacterial species.

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" processive exonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11–15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complementary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules,* ed. A G Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or wild type DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci. USA,* 75: 5765, 1978).

Cassette Mutagenesis

Another method for preparing variants, cassette mutagenesis, is based on the technique described by Wells et al. (*Gene,* 34:315, 1985). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. E.g., the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Throughput Methods for Screening Libraries of Peptide Fragments or Homologs Various techniques are known in the art for screening generated gene products. Techniques for screening large libraries often include cloning the nucleic acids of interest into replicable expression vectors, transforming appropriate cells with the resulting library of vectors, and expressing the genes under conditions in which detection of a desired activity, e.g., in this case, binding to a target organism or a surface component of a target organism, facilitates relatively easy isolation of the vector encoding the gene whose product was detected. Each of the techniques described below is amenable to high through-put analysis for screening large numbers of sequences created, e.g., by random mutagenesis techniques.

Display Libraries

In one approach to screening assays, the candidate peptides are displayed on the surface of a cell or viral particle, and the ability of particular cells or viral particles to bind an appropriate target organisms protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., target organisms, can be used to detect homologs which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd, and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loophotosensitizer of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080–1083). Surface proteins of other bacterial species have also served as peptide fusion partners. Examples include the Staphylococcus protein A and the outer membrane IgA protease of Neisseria (Hansson et al. (1992) *J. Bacteriol.* 174, 4239–4245; Klauser et al. (1990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al., 1992, *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B (Cull et al. (1992) *Proc. Natl. Acad. Sci. U.S.A.* 89–1869).

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are under-represented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357–364). To identify the sequences of the active peptides one sequences the DNA produced by the phagemid host.

Secondary Screens

The high through-put assays described above can be followed by secondary screens in order to identify, enrich and select for molecules having appropriate affinity for a biological entity. Secondary screens depend on the ability of the targeting moiety to bind a polymer of interest. For example, a surface protein or carbohydrate of the target organism of interest can be used to identify ligands from a group of peptide fragments isolated though one of the primary screens described above. One may use highly pure materials, for example, purified protein from a viral pathogen, obtained from a recombinant organism specifically obtained for the purpose of production of this material, or one may use a crude preparation of the target organism, such as a cell-wall or pellicle preparation, even a heat-inactivated or formalin-treated preparation of the target organism.

The Examples below illustrate two examples of targeting materials, a polyamino acid of positive charge, polylysine, which has affinity for a broad range of bacterial species and can also serve as a backbone for coupling of additional targeting moieties; and the salivary protein histatin, which has affinity for several species of oral bacteria. Each of these materials can be used as a starting material in the procedures described for phage display library, described herein, for example by incorporation of the nucleic acid sequence into that of gene III of the M13 phage display vector (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815). In this case, the target material for enrichment of the phage library may be bacterial cell wall fraction, isolated by sonication of the target organism in the cold in the presence of standard protease inhibitors, low speed centrifugation to separate cell walls from cytoplasm, and resuspension of wall material in buffer for use in several rounds of phage library binding selection. Procedures are described at length in U.S. Pat. No. 5,223,409. After two to three rounds of selection, phage bearing polyamino acid sequences or histatin variants of affinity to the target cell wall that is considerably enhanced over that of the starting material may be isolated. The sequence of the improved variants is readily determined by standard DNA sequence procedures, and the peptide can be produced in large quantity by standard peptide synthesis methods. Thus the procedures described here for generating fragments and analogs and testing them for enhanced affinity for the target organism are known in the art.

Target Organisms

Organisms to be targeted by the compositions and methods of the present invention are found on any light-accessible surfaces or in light-accessible areas, e.g., in human and animal subjects, on materials to be decontaminated, or on crop plants. In the cases of humans and animals, infections of the epidermis, oral cavity, nasal cavity, sinuses, ears, lungs, urogenital tract, and gastrointestinal tract are light accessible. Epidermal infections include those of unwanted organisms of bacterial, fungal, viral and animal origin, and include subcutaneous infections, especially localized lesions, for example caused by protozoans, parasites, or parasitic mites, which infections are light-accessible. Infections of the peritoneal cavity, such as those resulting from burst appendicitis, are light accessible via at least laparoscopic devices. A variety of skin infections which are refractory to antibiotics or long-term antifungal treatment, for example, dermatophycoses of the toenail, are suitable for PDT using the compositions of the invention.

A major area of application of compositions and methods of the invention are disorders and infections of the oral cavity, e.g., of the gums. Methods of the invention are particularly useful in treating oral infectious diseases, for example, periodontal diseases. Since pockets of periodontal disease infection occur within a few millimeters of the surface of the oral cavity, PDT offers significant advantages over the traditional physical methods of scaling and antibiotic therapy for this condition. Target oral unwanted organisms include a large number of bacterial and fungal species, e.g., Bacteroides species including *B. gingivalis* (now known as *Porphyromonas gingivalis*), *Eikenella corrodens, Fusobacterium nucleatum, Wolinella recta,* Eubacterium species, *Prevotella* (*Bacteroides*) *intermedia, Bacteroides forsythus,* Capnocytophaga species, *Actinobacillus actinomycetamcomitans,* and *Streptococcus mutans.*

Lung infection can occur with a variety of bacterial genera and species, which include the classical tuberculosis of *Mycobacterium tuberculosis,* the pseudomonads, which are the primary cause of death of cystic fibrosis patients, Klebsiella, and can also occur with a variety of virus strains. A variety of fungi and parasites are opportunistic pathogens of the lung, and *Pneumocystis carinii* infection is a common cause of death in immunocompromised AIDS patients. As pathogens of the lung are increasingly resistant to classical antibiotic therapies, PDT with the compositions of the instant invention offer an alternative method for eliminating these unwanted organisms that is independent of the microbial mechanisms of resistance. Additional epidermal infections and infections of deeper tissues arise from burns, scrapes, cuts, and puncture wounds. PDT with the compositions of the instant invention is useful for sterilization of such potential infectious sites, which can rapidly lead to toxic shock, a frequent concomitant of bullet wounds, and for treating the sites to eliminate or reduce unwanted infectious organisms. A major cause of infection in wounds, especially burns, is the Gram negative aerobic bacterium Pseudomonas. This organism produces an exotoxin which has been shown to retard wound healing. Multi-antibiotic resistant *P. aeruginosa* strains are becoming a significant problem, especially in burns units of large hospitals. Pseudomonads also produce fulminating infections of the cornea. *Escherichia coli* along with *Staphylococcus aureus* are the two most common bacteria in infected wounds.

Other sites of unwanted target organisms include the urogenital tract, the peritoneal cavity, the inner and outer ear, the nasal cavity and the gastrointestinal tract. Infectious sites of proliferation of unwanted target organisms in tissues of mesothelial and endothelial origin are also accessible to PDT by minimally invasive techniques.

Target organisms can be cellular or viral. Viruses which can be unwanted target organisms include any pathogenic life form comprising components of at least one nucleic acid molecule and one or more protein species, and may also include the enveloped viruses. Target organisms which are cells include at least a boundary cell membrane and are capable of energy production, nucleic acid synthesis, and contain ribosomes and are capable of ribosomal protein synthesis. Cells can be unicellular or multicellular, and said unicellular organisms can be prokaryotic or eukaryotic.

Prokaryotic target organisms can be bacteria, which bacteria can be Gram negative or Gram positive, or which are lacking cell walls. The Gram stain basis of distinguishing bacteria, based on whether or not cells of a specific strain or species of bacteria take up a stain, or are stained with the counterstain only, is known to those of skill in the art. Bacteria which are target organisms of the invention can be aerobic, anaerobic, facultatively anaerobic or microaerophilic. Spirochetes of the invention include but are not limited to the genera Borrelia and Treponema. This last genus contains species variously associated with the diseases of trenchmouth, pinta, and yaws, the latter two being tropical skin infections. Gram negative helical/vibroid motile bacterial genera suitable as target organisms include Campylobacter and Helicobacter. Gram negative aerobic and microaerophilic rods and cocci include the genera Bordetella, Neisseria, and Legionella. Facultatively anaerobic Gram negative rods include genera Pseudomonas, Salmonella, Shigella, Erwinia, Enterobacter, Erwinia, Escherichia, Vibrio, Haemophilus, Actinobacillus, Klebsiella and Salmonella. An important group of bacteria as target organisms for the present invention are the Gram positive cocci, including the genera Staphylococcus and Streptococcus, a strain of the latter known to cause a variety of infections including the childhood skin disease impetigo, and some strains of the former which are popularly designated, "flesh-eating bacteria." Gram positive rods include species of Listeria, suitable for treatment by the methods and compositions of the invention.

Bacteria suitable for photosensitizer composition treatment among those lacking rigid cell walls are the genus Mycoplasma. The actinomycete group includes several species of Mycobacterium that are suitable target organisms of the present invention. Additional bacterial genera which can be treated with the conjugate molecules of the invention include: Enterococcus, Leptospira, Serpulina, Mycoplasma, Bacteroides, Yersinia, Chlamydia, Vibrio, Actinobacillus, Porphyromonas, Hemophilus, Pasteurella, Peptostreptococcus, Propionibacterium, Corynebacterium and Dermatophilus. These and other bacterial groups and genera not listed here will be recognized by the skilled artisan as suitable target bacteria for the compositions of the invention.

Viruses that may be targeted by the compositions of the present invention include, but are not limited to, adenoviruses, herpesviruses, poxviruses, and retroviruses. Representative fungal target organism genera include but are not limited to, Cryptococcus, Blastomyces, Paracoccidioides, Candida, Aspergillus, Mycetoma, and include other genera causing various dermatomycoses.

Eukaryotic target organisms of the instant invention include unicellular protozoan and fungal pathogens and parasites, which can have a multicellular phase of the life cycle. Parasite infections of subjects are suitable for treatment by the compositions of the invention. Common parasites that infect or colonize the intestinal and urogenital tract include amoebae, flagellates, and nematodes. In addition, infection with trematodes, cestodes, ciliates, coccidian and microsporidian parasites may occur in these tracts. Members of the genera Leishmania and Onchocerca cause cutaneous ulcers, and of the genus Acanthamoeba can be found in corneal scrapings of the eye. *Leishmania donovani* causes the tropical ulcerating skin disease kala azar, which is suitable for treatment with the methods and compositions of the present invention. Intestinal tract genera that are suitable for targeting by compositions of the invention include Entamoeba, Giardia, Cryptosporidium, and microsporidia, pinworm, and helminth genera. Lung tissue can contain*Pneumocystis carinii,* and more rarely, amoebae such as Entamoeba, trematodes, or cestodes. The urogenital tract can be infected with Trichomonas, and with Schistosoma, which can be treated with compositions of the invention.

Viral, prokaryotic and eukaryotic target organisms are not limited to pathogens and parasites, and can include higher orders such as arthropods. Target organisms are not limited to pathogens and parasites of animal subjects, and can include plant pests.

These lists are used to illustrate applications of the present invention to major groups of suitable target organisms, but not to delimit the invention to the species, genera, families, orders or classes so listed.

Pharmaceutical Compositions

The compounds of the invention include conjugate molecules that have been formulated for topical administration, and also for administration to various external organs such as the outer ear, or organs accessible by external administration, such as by oral application or by lavage of the lung. The examples mentioned here are not intended as limiting with respect to the nature of the conjugate photosensitizer compositions of the invention, or to a particular route of the administration, and additional routes are listed herein. In another embodiment of the present invention, the photosensitizer compositions can be administered by combination therapy, i.e., combined with other agents. For example, the combination therapy can include a composition of the present invention with at least one other photosensitizer, at least one antibiotic, or other conventional therapy.

Photosensitizer conjugates that are somewhat insoluble in an aqueous solvent can be applied in a liposome, or a time release fashion, such that illumination can be applied intermittently using a regimen of periods of illumination alternating with periods of non-illumination. Other regimens contemplated are continuous periods of lower level illumination, for which a time-release formulation is suitable.

As used herein, the phrase "pharmaceutically acceptable carrier" includes any and all solvents, dispersion media, coatings, antibacterial and antifungal agents, isotonic and absorption delaying agents, and the like that are physiologically compatible. The use of such media and agents for pharmaceutically active substances is well known in the art. Preferably, the carrier is suitable for oral, intravenous, intramuscular, subcutaneous, parenteral, spinal or epidermal administration (e.g., by injection or infusion). Depending on the route of administration, the active compound may be coated in a material to protect the compound from the action of acids and other natural conditions that may inactivate the compound.

Conjugates of the invention can also be administered parenterally. The phrase "administered parenterally" as used herein means modes of administration other than oral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

One of ordinary skill in the art can determine and prescribe the effective amount of the pharmaceutical composition required. For example, one could start doses of the known or novel photosensitizer composition levels lower than that required in order to achieve the desired therapeutic effect and gradually increase the dosage until the desired effect is achieved.

Other Embodiments

The compositions of the invention can be used to decontaminate inanimate objects, such as medical and dental devices, heat-sensitive filters, surfaces of transilluminators, sonication probes, and any other surface that is light accessible and carries unwanted organisms. Many of these devices cannot be autoclaved, in which case the methods and compositions of the invention can be useful for decontamination.

The methods and compositions of the invention can be incorporated into a kit, which contain one or more of a photosensitizer which may or may not be coupled to a backbone, one or more target moieties, a coupling or cross-linking agent, buffers, and instructions for use. The user of the kit can select an appropriate target moiety to apply to the particular unwanted organism of choice. Two or more target moieties can be coupled to the photosensitizer-backbone, such that a broader range of unwanted organisms can be eliminated or substantially reduced by application of a single product.

The invention is further illustrated by the following examples, which should not be construed as further limiting. The contents of all references, pending patent applications and published patents, cited throughout this application, are hereby expressly incorporated by reference.

EXAMPLES

Example 1

Preparation of polylysine-chlorin e6 Conjugates of Varying Charges

Figure 1B:
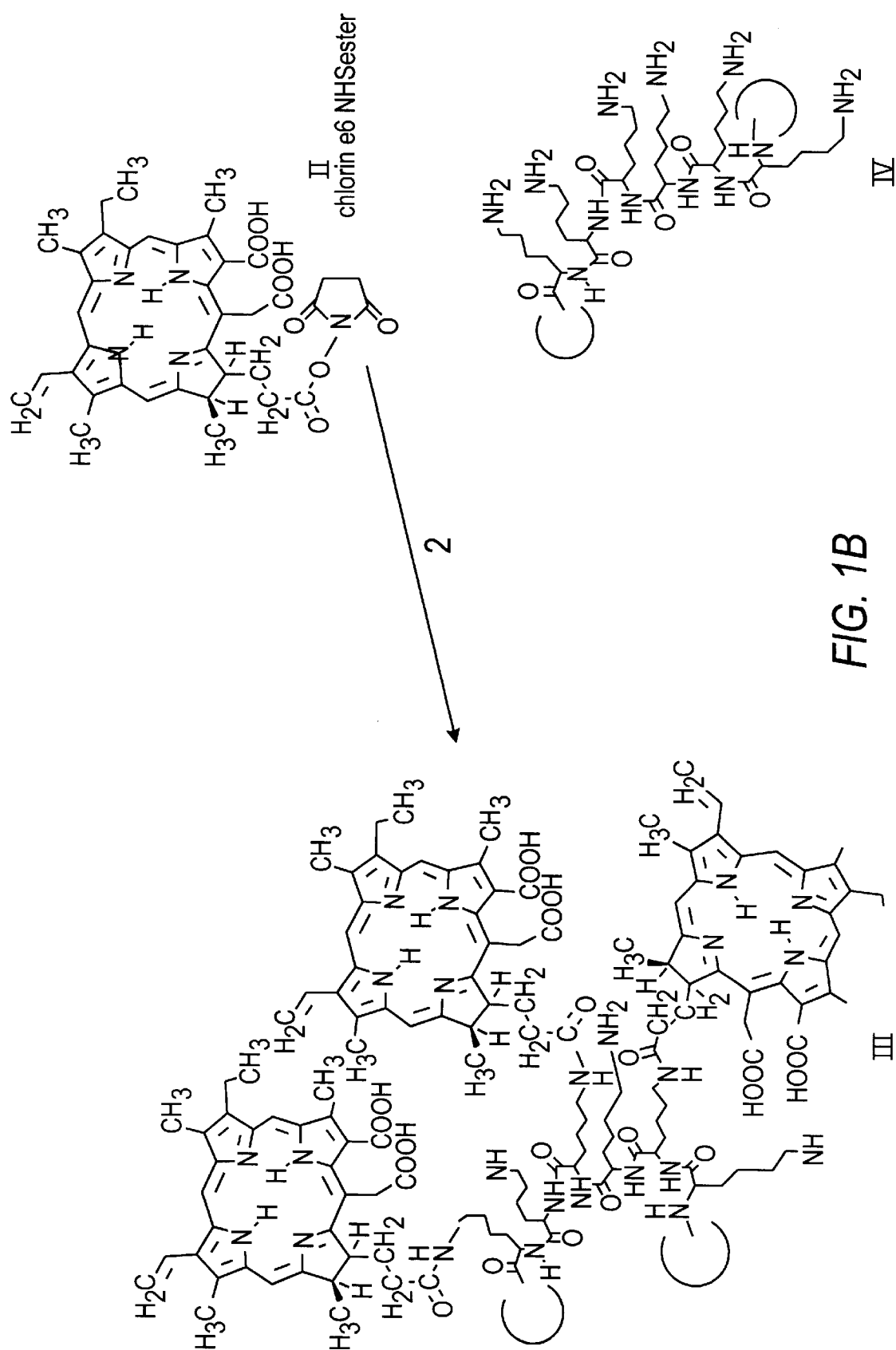
FIG. 1B is a diagram showing reaction 2 of molecule II with poly-L-lysine, molecule IV, to form poly-L-lysine chlorin e6, molecule III.

The N-hydroxy succinimide (NHS) ester of the photosensitizer chlorin e6, was prepared by reacting 1.5 equivalents of dicyclohexylcarbodiimide and 1.5 equivalents of NHS with one equivalent of chlorin e6, molecule I in FIG. 1A, or other photosensitizer in dry dimethylsulfoxide (DMSO) to form the NHS-ester, molecule II in FIG. 1A. The procedure described for the material prepared for use in these Examples, with the photosensitizer chlorin e6, is suitable also for preparation of esters of benzoporphyrin derivative, or any carboxyl containing tetrapyrrole photosensitizer. After incubation in the dark at room temperature for 24 h, the NHS ester was frozen in aliquots for further use. Poly-lysine (molecule III of FIG. 1B) hydrobromide (HBr, 50 mg) of either L or D optical configuration, and of a range of molecular weights (molecular weight 40,000 to 60,000, equivalent to 22,000 to 33,000 polylysine free base) was dissolved in 50 ml dry DMSO, and N-ethylmorpholine (1 ml) was added. To this solution was added dry DMSO (1 ml) containing photosensitizer-NHS ester (25 mg). The solution was incubated in the dark at room temperature for 24 h, to synthesize the polylysine chlorin e6 conjugate, molecule III in FIG. 1B, and also shown in FIG. 1C.

Charge modification was effected as follows.

To neutralize positive charges on the polylysine the molecules were reacted with an acylating agent, acetic anhydride. A sample of polylysine chlorin e6 conjugate (molecule III in FIG. 1D) solution was treated with an excess of acetic anhydride (100 mg dissolved in 0.5 ml dry DMSO) to produce an uncharged neutral acetic acid amide conjugate. The resulting molecule was uncharged. One can modify these conditions to produce molecules of other charges. This allows one to make and test various possibilities and choose the best for application to a particular conjugate or target organism.

To convert positive charges on the polylysine to negative charges, the molecules were reacted with an acylating agent, succinic anhydride. A sample of the polylysine chlorin e6 in DMSO was treated with an excess of succinic anhydride (100 mg dissolved in 0.5 ml dry DMSO) to produce the succinic acid amide, and convert the positively charged amino groups to negatively charged carboxylic acid groups. The resulting molecule had all lysines converted to negative charges. One can modify the conditions to produce molecules of other charges. This would allow one to make and test various possibilities and choose the best for application to a particular conjugate or target organism.

Figure 1C:
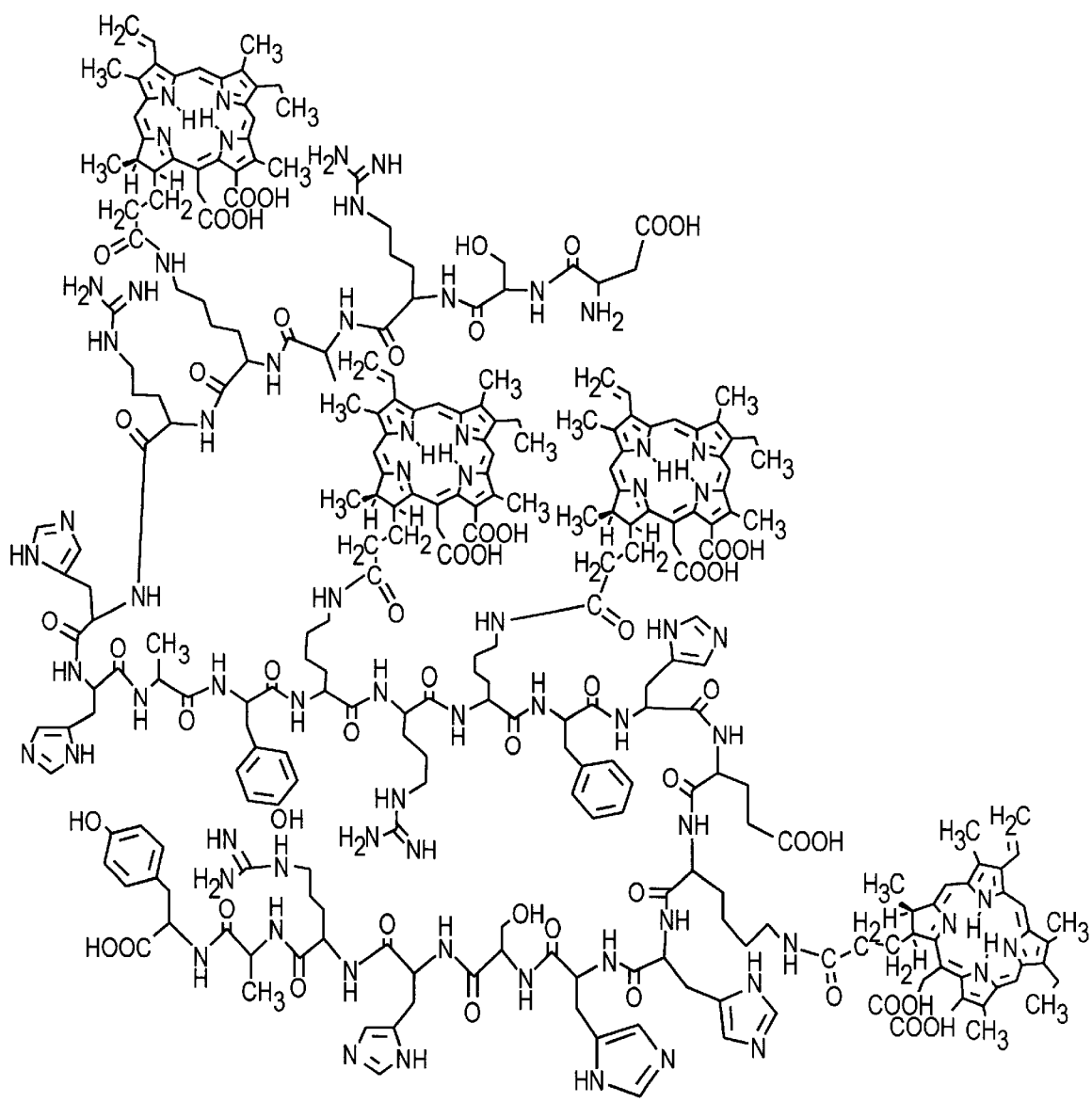
FIG. 1C is a diagram showing the chemical structure of histatin-5 chlorin e6 conjugate, with four chlorin e6 moieties each coupled to an ϵ-amino group of each lysine residue of histatin-5.
Figure 1D:
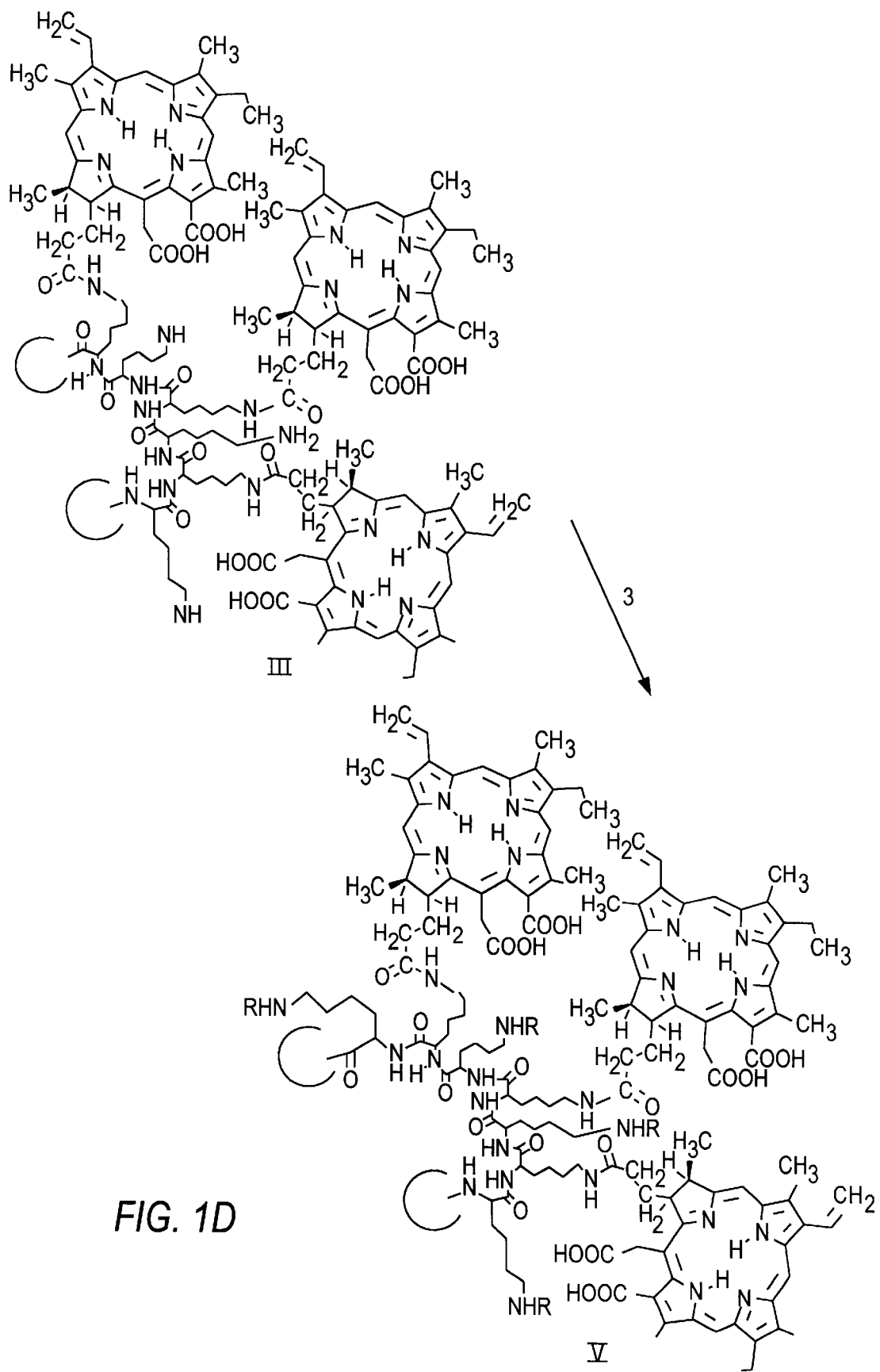
FIG. 1D is a diagram showing the reaction of molecule III with acetic anhydride or succinic anhydride in DMSO to form two species of molecule V, which for chlorin e6 polylysine acetic acid amide neutral conjugate the R group indicates —$COCH_3$, and for chlorin e6 polylysine succinic acid amide the R group indicates —$COCH_2CH_2COOH$; for molecule III that is not further acylated, the R group in species V is —H.

After incubation of the conjugated molecules, and the acylated charge-modified conjugates, in the dark at room temperature for 24 h, the solutions were transferred to dialysis tubes having the correct molecular weight cutoff to permit dialysis of polylysine, using dialysis material resistant to DMSO, and dialyzed for 24 h against 3 changes of 10 mM phosphate buffer (pH 7). FIG. 1D shows molecule V, which for chlorin e6 polylysine acetic acid amide neutral conjugate the R group indicates —$COCH_3$, and for chlorin e6 polylysine succinic acid amide the R group indicates —$COCH_2CH_2COOH$.

Example 2

Preparation of histatin-chlorin e6 Conjugates of Varying Charges

Histatin-5 (10 mg) was dissolved in 2 ml of 0.1 M $Na_2CO_3$ buffer, pH 9.5, and was mixed with 0.1 ml DMSO containing 5 mg of chlorin e6 N-hydroxysuccinic amide, prepared as described in Example 1. The reaction was continued further by incubation for 24 h at room temperature in the dark, and the solution was dialyzed three times against 10 liters of PBS. The resulting green precipitate was dissolved in 2 ml 0.1 M $Na_2CO_3$ buffer, pH 10.5.

Measurements of the absorbance spectrum indicated that, assuming the extinction coefficient at 400 nm of chlorin e6 was unchanged by complexation, i.e., is $1.5 \times 10^5$ $M^{-1}$, $cm^{-1}$, and that all chlorin e6 remaining after dialysis was covalently attached to the histatin, it was determined that 4 chlorin e6 molecules were attached per histatin-5 peptide chain. Although histatin-5 is basic, the conjugate was found to be acidic, since lysine amino groups were replaced with two carboxyl groups on the chlorin. The structure is shown in FIG. 1C.

The ratio of histatin to chlorin e6 can be varied by altering the ratio of the two species in the reaction.

Example 3

Figure 2A:
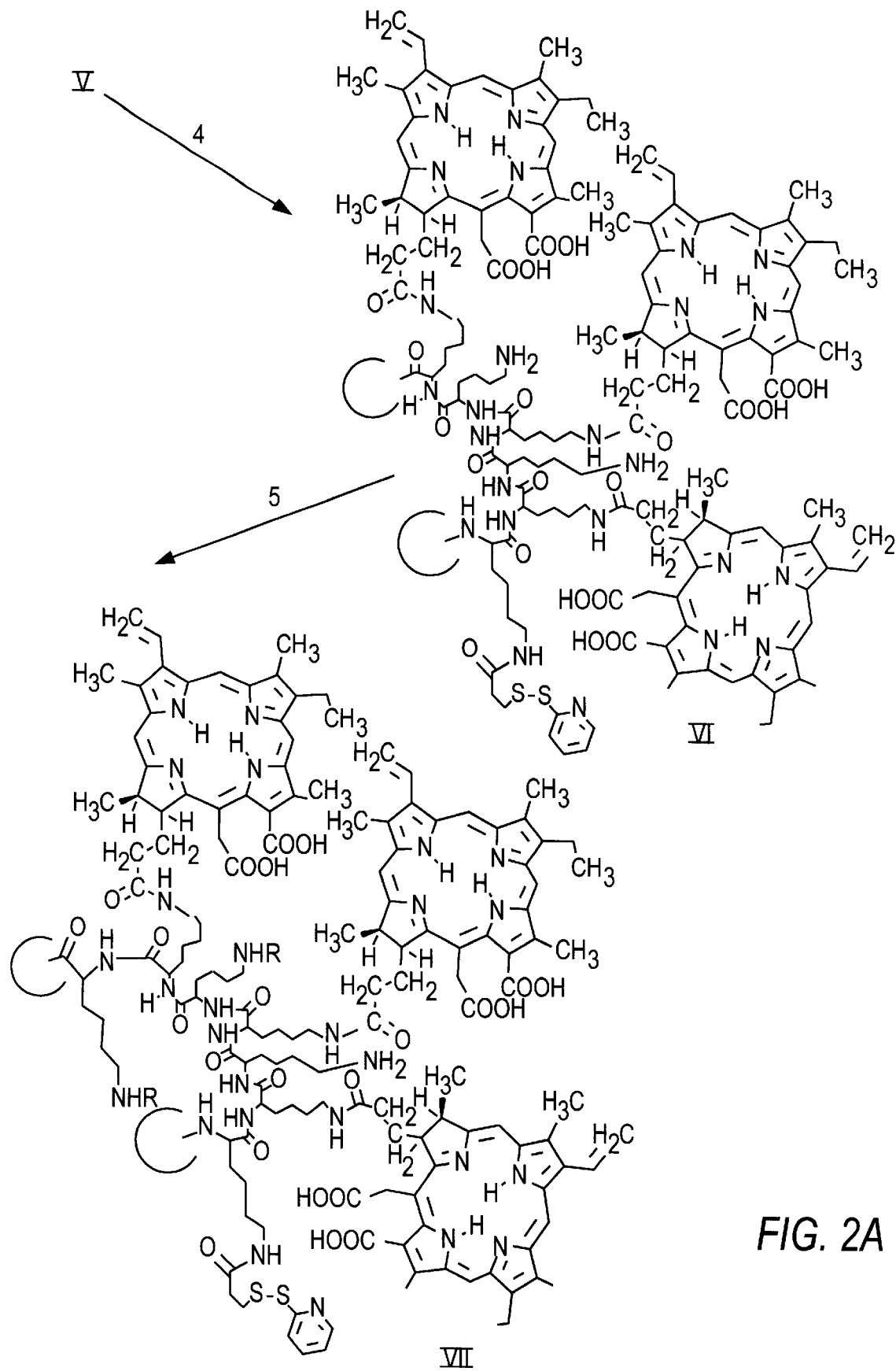
FIG. 2A is a diagram of the first reaction sequences for synthesis of cationic, neutral and anionic chlorin e6 polylysine conjugates with a histatin-5 16 amino acid residue fragment, by synthesis of molecules containing the sulfhydryl reactive functional group 2-pyridyl-dithio-3-propionyl, with reaction 4 showing molecule V, polylysine-chlorin e6, reacting with N-succinimidyl-3-[2-pyridyldithiol] propionate (SPDP) in DMSO to produce polylysine-chlorin e6-SPDP, molecule VI, and with further reaction 5 of molecule VI with acetic anhydride or succinic anhydride in DMSO to produce the acetyl and succinyl derivatives, where R in molecule VII indicates —$COCH_3$ and —$COCH_2CH_2COOH$, respectively.

Preparation of histatin-polylysine-chlorin e6 Conjugates of Varying Charges The DMSO solution of polylysine-chlorin e6 referred to in Example 1 was treated with a solution of N-succinimidyl-3-[2-pyridyldithiopropionate] (SPDP) in DMSO to form polylysine chlorin e6-SPDP, Molecule VI in FIG. 2A. The amount depends on the molecular weight of the polylysine but should be about three to four equivalents per polymer chain. The reaction is incubated for 24 h in the dark at room temperature. The polylysine-photosensitizer-SPDP solution is dialyzed as above.

Figure 2B:
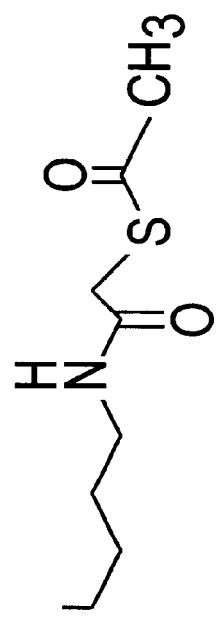
FIG. 2B is a diagram that shows further reactions of molecules of VII and of a 16 amino acid residue fragment of human histatin-5 to synthesize the conjugate, with reaction 6 showing reaction of the histatin-5 fragment with SATA to produce SATA-histatin-5 fragment, molecule IX, which is then deprotected by hydroxylamine in reaction 7 to produced deprotected SATA coupled to histatin-5 fragment, molecule X.
Figure 2B:
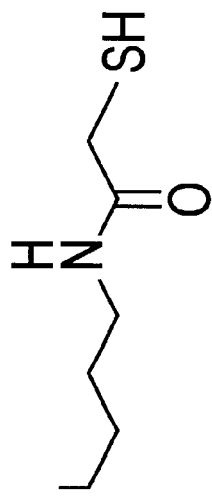

The histatin (or other polypeptide containing at least one lysine residue, 5 mg) is dissolved in 2 ml phosphate buffer (SATA, 50 mM, pH 7.5 containing 1 mM EDTA) and treated with N-succinimidyl-S-thioacetate (0.5 mg dissolved in DMSO, 100 µl) for 1 h at room temperature as shown in reaction 6 of FIG. 2B, to form SATA-histatin, molecule IX in FIG. 2B The solution of the peptide is then treated with 200 µl of a solution containing hydroxylamine hydrochloride 0.5 mM, EDTA 25 mM and sodium phosphate 50 mM, pH 7.5, and incubated for 2 h at room temperature to form the deprotected SATA derivative, molecule X in FIG. 2B. The solution is then desalted on a P4 column, and eluted with phosphate buffer (50 mM, pH 7.5) containing 10 mM EDTA. This results in the production of a peptide containing free thiol group.

Figure 2C:
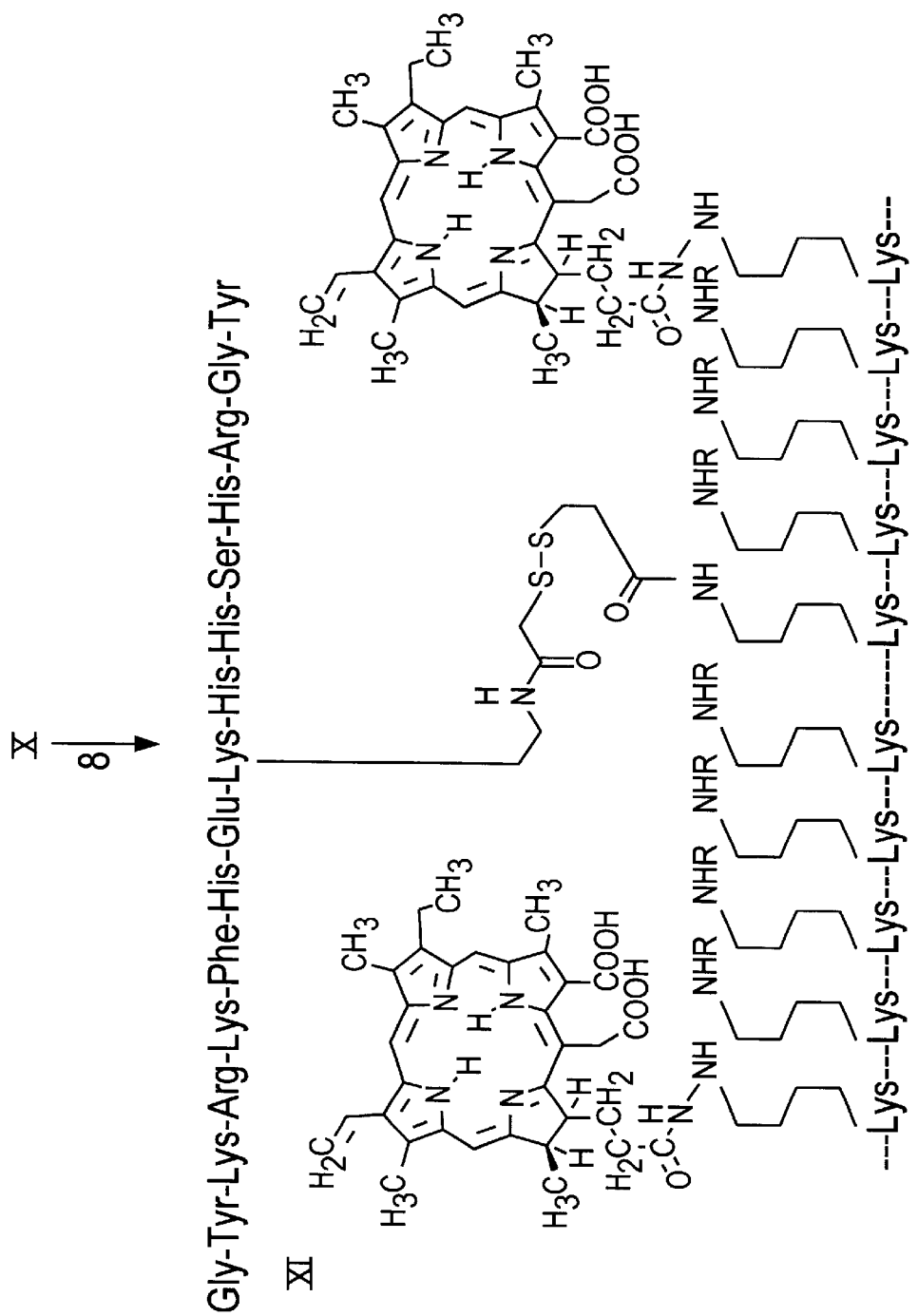
FIG. 2C is a diagram showing reaction 8 of molecule X which is here coupled to each of the polylysine-chlorin e6 molecules and acetyl and succinyl derivatives of molecule VII, to produce the molecular species in XI, where R indicates —H for the positively charged unacylated conjugate, R indicates —$COCH_3$ for the neutral acetic acid amide, and R indicates —$COCH_2CH_2COOH$ for the negatively charged succinic acid amide.

The peptide containing free thiol group derivative of polylysine chlorin e6, molecule VII in FIG. 2A, which can be positively, neutrally or negatively charged, is then reacted with the SPDP in the ratio of the relative molecular weight of peptide and polylysine, for 24 h at room temperature. The product comprising a peptide-polylysinechlorin e6 conjugate shown in FIG. 2C is then purified on a Sephadex G50 column.

Example 4

Photosensitizer chlorin e6 Conjugate Uptake

*Porphyromonas gingivalis* 381, a Gram negative bacterium and one of the most common species in dental plaque, was maintained by weekly subculture in Trypticase Soy Agar (TSA) with 1% hemin, 1% vitamin K and 5% sheep blood. For experimental purposes, the organism was grown anaerobically in a chamber with 80% $N_2$, 10% $CO_2$ at 35° C. for 48 h, harvested by centrifugation and resuspended in Trypticase Soy Broth (TSB) with 1% hemin and 1% vitamin K. Cells were dispersed by sonication and repeated passage through Pasteur pipettes. Cell numbers were measured in a spectrophotometer (at wavelength 600 nm, in which an O.D. of 1 yields $10^8$ cells/ml) using one ml tubes, to obtain the appropriate number of bacteria for each experiment ($10^9$ cells/ml for uptake studies and $10^8$ cells/ml for irradiation studies).

Hamster cheek pouch squamous cell carcinoma cell line (HCPC-1) cells were used (Odukoya, O. et al., JNCI 71:6, 1253–1258, 1983). Cells were grown in Dulbecco's modified Eagle's medium (DMEM) with high glucose (Gibco, Grand Island, N.Y.) supplemented with heat-inactivated 10% fetal calf serum (FCS, Gibco), 100 units/ml penicillin G and 100 µg/ml streptomycin (Sigma, St. Louis, Mo.). Medium was changed every 2–3 days and cells were passaged weekly using trypsin-EDTA. All cells were maintained in 10 cm-diameter culture dishes with 12 ml growth medium at 37° C. in a humidified, 95% air, 5% $CO_2$ atmosphere.

The following photosensitizing conjugates of the invention of poly-1-lysine with chlorin e6 (M. Wt. 1,000 to 3,000) with positive, negative and neutral charges, were used: polylysine chlorin e6 (cationic, unacylated); polylysine chlorin e6-succinylated (anionic, polylysine-chlorin e6-succ); and polylysine chlorin e6 acetylated (neutral, polylysine-chlorin e6-ac). Synthesis is described in Example 1. Unless indicated, all media, buffers, solutions, and glassware used for growth and maintenance of bacterial and animal cells were sterile.

Samples of suspensions of *P. gingivalis* ($10^9$ cells/ml) were incubated in triplicate in the dark at room temperature for one min with photosensitizer at 1, 5 and 10 µm chlorin e6 equivalent (final concentration in TSB). Cell suspensions were centrifuged, the photosensitizer-containing supernatants aspirated and bacteria were washed once with 1 ml sterile PBS. Cells were resuspended in 1.5 ml 0.1 M NaOH/1% sodium dodecyl sulfate (SDS), and incubated for at least 24 h to yield a homogenous solution.

Fluorescence of each cell extract was measured on a spectrofluorimeter (model FluoroMax, SPEX Industries, Edison, N.J.). The excitation wavelength was 400 nm and emission spectra of cell suspensions were recorded from 580 to 700 nm. The protein content of each cell extract was determined by a modified Lowry method (Markwell M. A. et al. *Anal. Biochem.* 87:206, 1978) using bovine serum albumin dissolved in 0.1 M NaOH/1% SDS as a protein standard to construct calibration curves. Results were expressed as mol chlorin e6 taken up per mg cell protein.

HCPC-1 cells in exponential growth phase were trypsinized and counted using a hemocytometer. Each well of 24-well culture plates was seeded with $10^5$ cells in 1 ml growth medium containing 10% FCS, and were incubated overnight to allow cells to attach and resume exponential growth. Conjugates were added to wells in triplicate, as follows. Medium was removed and replaced with medium containing 10% FCS and the conjugates at concentrations indicated, and plates were incubated for 1 min. The conjugate solutions were then aspirated from wells, cells were washed once with 1 ml sterile PBS, and incubated with 1 ml trypsin-EDTA for 10 min. The resulting cell suspensions were centrifuged, the trypsin supernatant was aspirated and pellets were dissolved in 0.1 M NaOH/1% SDS. Fluorescence of each cell extract was determined as described above.

Figure 3:
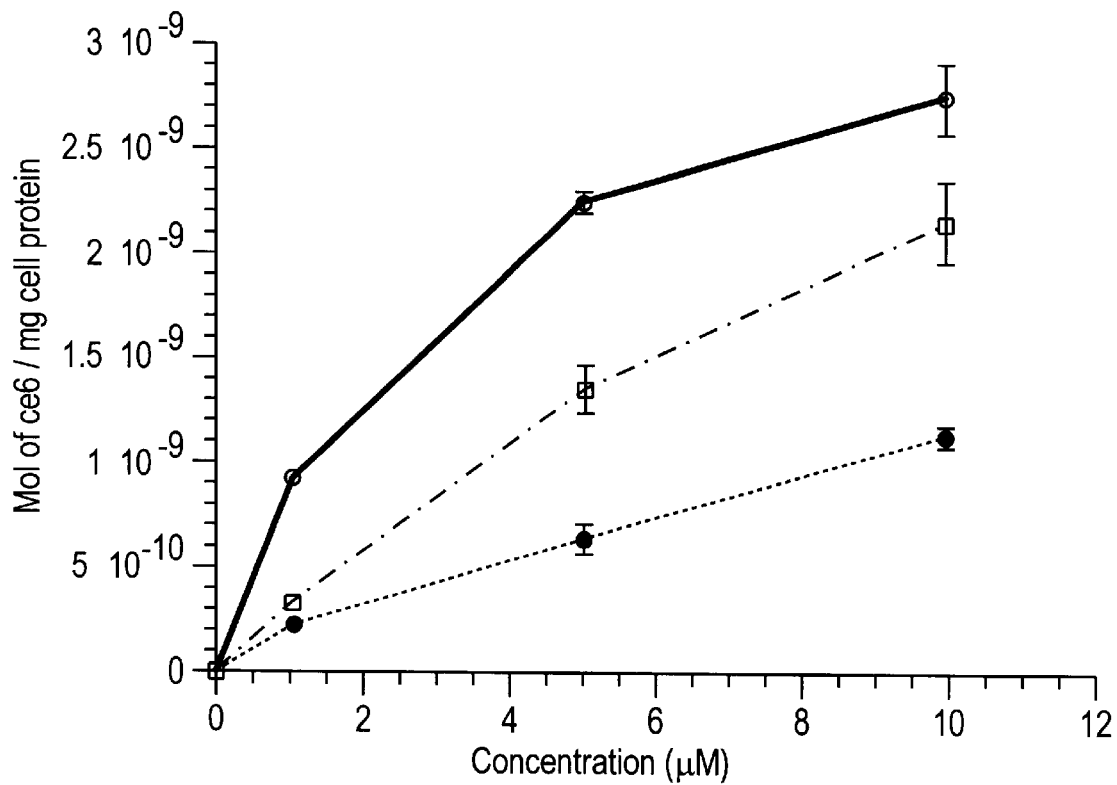
FIG. 3 is a graph of uptake of three polylysine chlorin e6 conjugates, in $10^{-9}$ mol of chlorin e6 per mg of cell protein by cells of Porphyromonas gingivalis, with uptake of the cationic conjugate shown by the solid line connecting circles, uptake of the anionic succinylated conjugate shown by the dashed line connecting squares, and uptake of the neutral acetylated conjugate shown by the dotted line connecting solid circles, as a function of chlorin concentration in $\mu$M.
Figure 4:
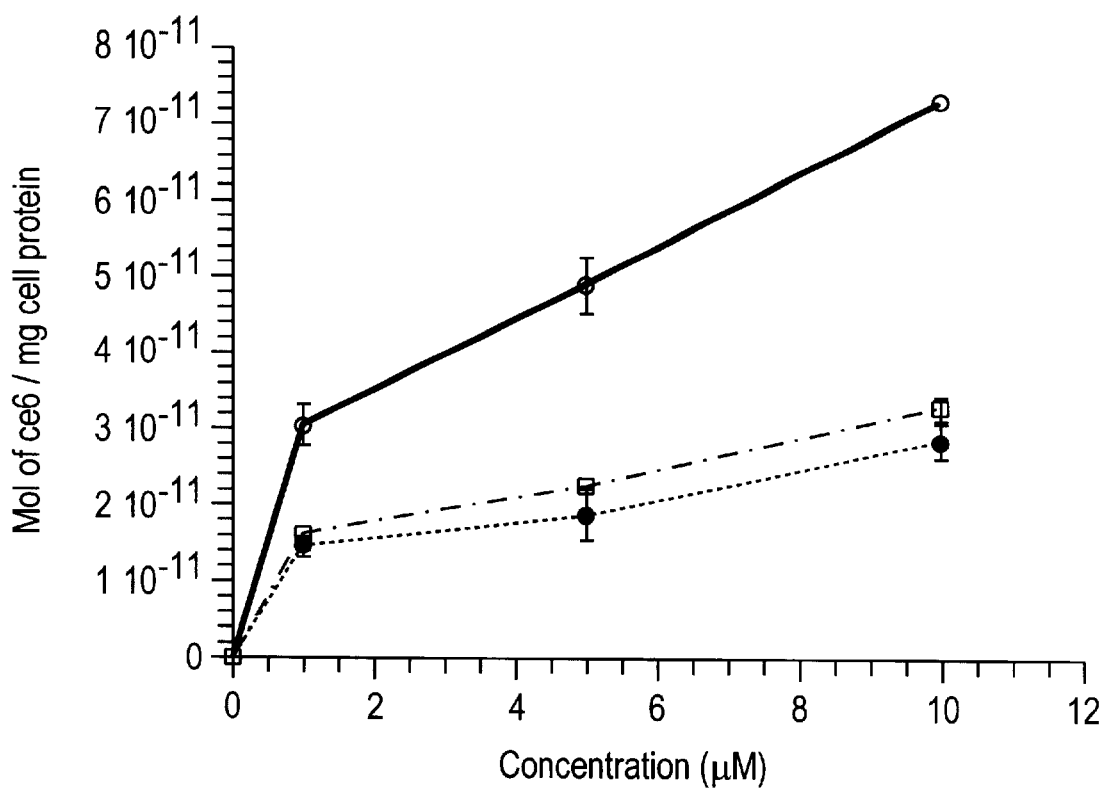
FIG. 4 is a graph of uptake of the three chlorin e6 conjugates, in $10^{-11}$ mol of chlorin e6 per mg of cell protein by cells of HCPC-1 hamster cheek pouch squamous cell carcinoma cells as a function of chlorin concentration in $\mu$M, with symbols representing each conjugate as described in the legend to FIG. 3.

The uptake of conjugates as a function of concentration is shown in FIGS. 3 and 4, for *P. gingivalis* and HCPC-1 cells, respectively (ordinates in these Figures differ by a factor of 50). Uptake of chlorin e6 conjugates was dose-dependent. Cells of *P. gingivalis* and HCPC-1 cells accumulated 2 and 2 to 4 times more, respectively, of the cationic conjugate compared to the anionic and neutral conjugates, at each concentration. A high degree of selectivity of accumulation of these photosensitizer conjugates into bacteria, compared to that for mammalian cells, is observed.

Example 5

Phototoxicity of e6 Conjugates

In order to establish the effectiveness and selectivity of these conjugates for killing bacteria while sparing mammalian cells, the three conjugates were compared to two widely used clinical photosensitizers, Photofrin II and benzoporphyrin derivative (BPD) (QLT Phototherapeutics Inc., Vancouver, BC). Photosensitizer bulk solid was dissolved in DMSO at 1 mM and diluted in TSB.

Suspensions of *P. gingivalis* cells ($10^8$/ml) were incubated in duplicate in the dark at room temperature for 1 min with 5 µm chlorin e6 equivalent of each conjugate, with Photofrin II, and with BPD. Cells were centrifuged, washed once with sterile PBS, and 1 ml fresh TSB was added. In the Example here, the ratios of uptake of chlorin e6 per mg cell protein in *P. gingivalis* and HCPC-1 cells for the cationic, anionic and neutral conjugates were 46:1, 60:1 and 22:1, respectively.

Bacterial suspensions were added to wells of 12-well plates, and were irradiated in the dark at room temperature using a light emitting diode array which emitted light with wavelengths from 630–710 nm, spanning the absorbance maxima of these photosensitizer compositions. Wells were exposed from below, using fluences from 0 to 25 J/cm$^2$ at an irradiance of 65 mW/cm$^2$. Plates were covered during illumination to maintain sterility of the cultures. After illumination of the appropriate wells, serial dilutions of the contents of each well were prepared in TSB, and duplicate 100 µl aliquots were spread on the surfaces of blood agar plates. Survival fractions in each well were calculated by counting the colonies on the plates and dividing by number of colonies from unirradiated controls incubated with photosensitizer in the dark at room temperature for periods equal to irradiation times. Other controls were: bacteria treated neither with photosensitizer nor light, and incubated at room temperature in the dark, and cells exposed to light in the absence of photosensitizer.

HCPC-1 cells, $2 \times 10^4$ in aliquots of 100 µl growth medium with 10% FCS, were seeded in 96-well plates and cultured for 24 h until 70% confluent. Six wells from each plate were incubated with 5 µM of each photosensitizer and irradiated using the conditions described in Example 3. After illumination, cells were incubated with fresh medium at 37° C. for 24 h. Control cells were incubated under the conditions as in Example 3. Cell viability was determined 24 h after irradiation using the MTT-microculture tetrazolium assay, a method that assesses dehydrogenase activity in mitochondria of live cells (Mosmann T. J. Immunol. Methods 65, 55–63, 1983), and survival fractions were calculated as 570 nm absorbance of treated cells divided by that of unirradiated controls.

Figure 5:
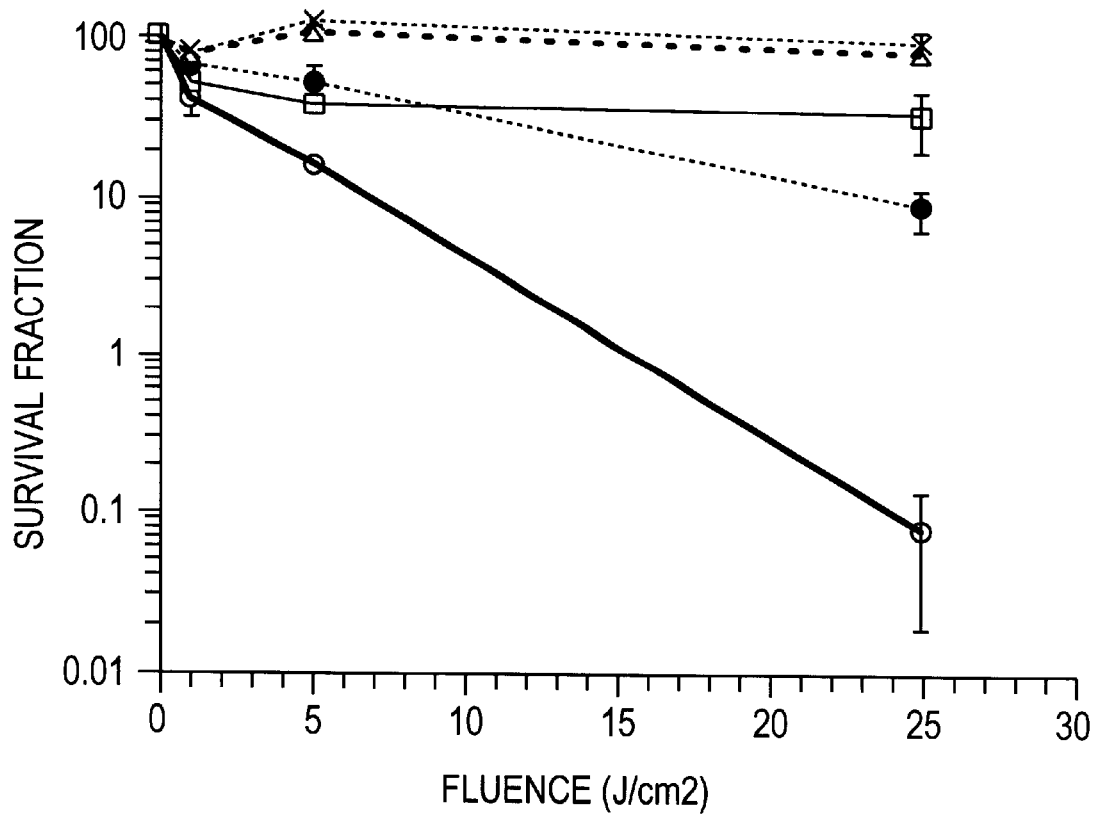
FIG. 5 is a graph of survival of P. gingivalis cells following irradiation by light of wavelength 630–710 nm, the cells previously having taken up chlorin e6 conjugates according to the symbols indicated in the legend to FIG. 3, with an additional cell sample having taken up Photofrin II (shown by a dashed line connecting the x symbols), and another cell sample having taken up benzoporphyrin derivative (shown by a dashed heavy line connecting solid triangles), as a function of fluence of light.
Figure 6:
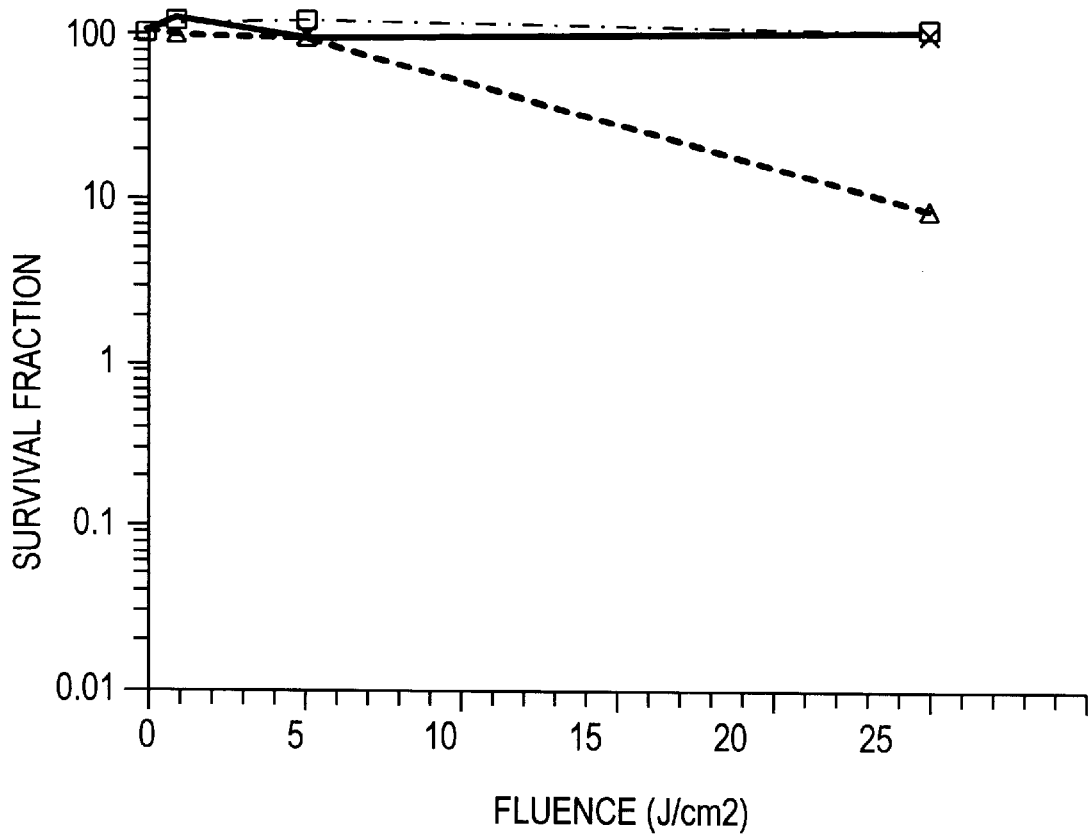
FIG. 6 is a graph of survival of HCPC-1 hamster squamous cell carcinoma cells following irradiation by light of wavelength 630–710 nm, cells previously having taken up chlorin e6 conjugates as indicated by the symbols in FIGS. 3 and 6, as a function of fluence of light.

FIGS. 5 and 6 show that the conjugates are highly selectively phototoxic to *P. gingivalis* compared to mammalian cells. The cationic conjugate polylysine-chlorin e6 killed 99.9% of bacteria, and less than 2% of HCPC-1 cells. High selectivity of the neutral conjugate, polylysine-chlorin e6-ac, which killed over 90% of bacteria and not HCPC-1 cells, is also shown. The anionic conjugate polylysine-chlorin e6-succ caused a 66% reduction in viability of *P. gingivalis*, and HCPC-1 cells were not killed by this photosensitizer.

In contrast, PFII and BPD did not show killing at the indicated concentrations, except for BPD which killed HCPC-1 cells and not *P. gingivalis*.

Example 6

In Vivo Studies in Animal Wound Models

Infected wounds are created on the dorsal skin of mice by using a scalpel to produce a 3 cm incision which is then inoculated with $10^7$ and $10^8$ c.f.u. of a bacterial species. An infected bum is produced as described by Stevens, E. J. et al., J. Burn. Care Rehabil. 15, 232–235, 1994. Conjugates directed against either of the bacterial species or unconjugated chlorin e6 are injected either perilesionally or intravenously. The doses of conjugate, light, and the interval between the injection and illumination are varied systematically. Responses to treatment are assessed by observing the rate of healing of the wound and the burn. Tissue samples (2 mm punch biopsies) are taken at intervals after treatment to determine the quantity the bacteria, and to provide slides for histopathological evaluation. Bacterial colonization in wounds is quantitated by establishing c.f.u./g tissue, and by optical monitoring of the luciferase transfected *P. aeruginosa* bacterial strain.

OTHER EMBODIMENTS

Where a value for a physical parameter, e.g., molecular weight or number of amino acid residues is given herein, the values can describe a population of molecules all or substantially all of which exhibit that value or, to a population of molecules wherein the value represents an average, mean, or mode value for that parameter for the population. The specification of a physical parameter, e.g., the size of a peptide or protein polymer, by number of residues or by molecular weight, can include the possibility of a degree of heterogeneity in the number of residues or in the molecular weight, such as occurs in the process of chemical synthesis of such polymers and which can be reduced but not generally entirely eliminated by purification processes prior to further use. Thus, for example, a preparation of polylysine indicated as being comprised of 10 lysine residues may consist of 80%, 90%, 95%, 99% or 99.9% of the molecules being of this length, with the remaining 20%, 10%, 5%, 1% or 0.1% of molecules having for example 9 or 8 residues, or more rarely, 11 or 12 residues.

The conjugates described herein can be synthesized by substituting a mixed population for one or more of the moieties discussed herein. For example, a pure preparation of a single photosensitizer moiety may be added to a reaction mix containing a mixture of backbone or targeting moiety substrates, to produce conjugates which include a single type of photosensitizer moiety conjugated to a mixture of targeting moieties, or to a mixture of backbone or targeting moiety chemical entities.

With regard to conjugates described herein a mixture may be constituted in a formulation of the conjugate prior to use, for example, a formulation intended for application to a mixture of unwanted organisms may be prepared as a mixture of two or more conjugates, each conjugate having an optimal affinity for one or more unwanted organisms, such that a plurality of target organisms can be reduced or eliminated.

The invention also includes fragments, preferably biologically active fragments, or analogs of a histatin, for example, histatin-5. A biologically active fragment or analog is one having any in vivo or in vitro activity which is characteristic of the histatin sequence. Particularly preferred fragments are fragments, e.g., active fragments, which are generated by de novo synthesis, proteolytic cleavage or alternative splicing events. Because peptides such as histatins often exhibit a range of physiological properties and because such properties may be attributable to different portions of the molecule, a useful histatin fragment or histatin analog is one which exhibits a biological activity in any biological assay for histatin activity. Most preferably the fragment or analog possesses at least 20% of the activity of the full-length naturally occurring histatin in any in vivo or in vitro histatin assay.

Analogs can differ from naturally occurring histatin in amino acid sequence or in ways that do not involve sequence, or both. Non-sequence modifications include in vivo or in vitro chemical derivatization of histatin. Non-sequence modifications include changes in acetylation, methylation, phosphorylation, carboxylation, or glycosylation.

Preferred analogs include histatin (or biologically active fragments thereof) whose sequences differ from the wild-type sequence by one, two, three, four, or five or more conservative amino acid substitutions and/or by one, two, three, four, or five or more non-conservative amino acid substitutions, deletions, or insertions which do not abolish the histatin biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to a histatin analog, will ordinarily be of sufficient length to confer biological activity, e.g., at least 20% of the binding activity of a full length molecule. In preferred embodiments the fragments are 12 residues long or longer. Fragments of a histatin can be generated by methods described herein and by methods known to those skilled in the art. The ability of a candidate fragment to exhibit a biological activity of histatin can be assessed by methods known to those skilled in the art and as described herein.

In order to obtain a histatin polypeptide, histatin-encoding DNA can be introduced into an expression vector, the vector introduced into a cell suitable for expression of the desired protein, and the peptide recovered and purified, by prior art methods. Preferably histatin peptides are produced in vivo as a fusion to a larger protein, and are cleaved into the fragment after initial purification from a cell extract. Preferably the histatin peptides are synthesized chemically, for example, on a peptide synthesizer.

TABLE 1

CONSERVATIVE AMINO ACID REPLACEMENTS

| For Amino Acid | Code | Replace with any of |
|---|---|---|
| Alanine | A | D-Ala, Gly, beta-Ala |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | none in parent therefore use is not preferred |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, |
| Leucine | L | D-Leu, Val, D-Val, Leu, D-Leu |
| Lysine | K | D-Lys, Arg, D-Arg, homo-Arg, D-homo-Arg, Ile, D-Ile, Orn, D-Orn |
| Methionine | M | none in parent therefore use is not preferred |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D-or L-1-oxazolidine-4-carboxylic acid |
| Serine | S | D-Ser, Thr, D-Thr, allo-Thr, phosphoser |

TABLE 1-continued

CONSERVATIVE AMINO ACID REPLACEMENTS

| For Amino Acid | Code | Replace with any of |
|---|---|---|
| Threonine | T | D-Thr, Ser, D-Ser, phosphoser, allo-Thr, Val, D-Val |
| Tyrosine | Y | D-Tyr, Phe, D-Phe, L-Dopa, His, D-His |
| Valine | V | D-Val, Leu, D-Leu, Ile, D-Ile |

Preferred histatin-1 analogs are those in which:
R1 is asp or is deleted
R2 is ser or phosphoserine or is deleted
R3 is his or is deleted
R4 is ala or is deleted
R5 is lys or arg or glu or asp
R6 is arg or lys
R7 is his
R8 is his
R9 is gly or ala
R10 is tyr or phe
R11 is lys or arg
R12 is arg or lys
R13 is lys or arg
R14 is phe or tyr
R15 is his
R16 is glu or asp
R17 is lys or arg
R18 is his
R19 is his
R20 is ser or thr or phosphoser
R21 is his or is deleted
R22 is arg or lys or is deleted
R23 is gly or glu or asp or is deleted
R24 is tyr or phe or is deleted
R25 is pro or arg or lys or is deleted
R26 is phe or tyr or leu or ile is deleted
R27 is phe or tyr or leu or ile or thr or ser or is deleted
R28 is gly or ala or is deleted
R29 is asp or glu or is deleted
R30 is phe or tyr or leu or ile or is deleted
R31 is gly or ala or is deleted
R32 is deleted or ser or thr or phosphoser
R33 is deleted or asn or gln
R34 is deleted or tyr or phe
R35 is deleted or leu or ile or tyr or phe
R36 is tyr or phe or leu or ile or is deleted
R37 is deleted or asp or glu
R38 is deleted or asn or gln Preferred histatin-3 analogs are those in which:
R1 is asp or is deleted
R2 is ser or phosphoserine or is deleted
R3 is his or is deleted
R4 is ala or is deleted
R5 is lys or arg or glu or asp
R6 is arg or lys
R7 is his
R8 is his
R9 is gly or ala
R10 is tyr or phe
R11 is lys or arg
R12 is arg or lys
R13 is lys or arg
R14 is phe or tyr
R15 is his
R16 is glu or asp
R17 is lys or arg
R18 is his
R19 is his
R20 is ser or thr or phosphoser
R21 is his or is deleted
R22 is arg or lys or is deleted
R23 is gly or glu or asp or is deleted
R24 is tyr or phe or is deleted
R25 is arg or lys or is deleted
R26 is deleted or ser or thr or phosphoser
R27 is deleted or asn or gln
R28 is deleted or tyr or phe
R29 is deleted or leu or ile or tyr or phe
R30 is tyr or phe or leu or ile or is deleted
R31 is deleted or asp or glu
R32 is deleted or asn or gln Preferred histatin-5 analogs are those in which:
R1 is asp or is deleted
R2 is ser or phosphoserine or is deleted
R3 is his or is deleted
R4 is ala or is deleted
R5 is lys or arg or glu or asp
R6 is arg or lys
R7 is his
R8 is his
R9 is gly or ala
R10 is tyr or phe
R11 is lys or arg
R12 is arg or lys
R13 is lys or arg
R14 is phe or tyr
R15 is his
R16 is glu or asp
R17 is lys or arg
R18 is his
R19 is his
R20 is ser or thr or phosphoser
R21 is his or is deleted
R22 is arg or lys or is deleted
R23 is gly or glu or asp or is deleted
R24 is tyr or phe or is deleted In preferred embodiments the targeting moiety includes a histatin, or an active fragment or analog thereof, e.g., histatin-1 through -8, preferably histatin-1, -3, or -5. In preferred embodiments the targeting moiety includes a fragment of a histatin, e.g., histatin-5. In preferred embodiments the targeting moiety includes histatin-5 residues 13–24, or corresponding residues from other histatins. In preferred embodiments the targeting moiety includes a histatin molecule which has been engineered to include an internal duplication.

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

What is claimed is:

1. A method of treating a subject for a disorder of the oral cavity characterized by the presence of an unwanted organism comprising: administering to the subject, a conjugate comprising a polylysine backbone to which is coupled a histatin targeting moiety and a porphyrin photosensitizer; irradiating the subject with energy of a wavelength appropriate to produce a cytotoxic effect by the photosensitizer; thereby treating the subject, for the disorder characterized by the presence of an unwanted organism.

2. A method of treating a subject for a disorder of the oral cavity characterized by the presence of an unwanted organism comprising: administering to the subject, a polycationic photosensitizer conjugate comprising chlorin e6 coupled to polylysine; irradiating the subject with energy of a wavelength appropriate to produce a cytotoxic effect by the photosensitizer; thereby treating the subject, for the disorder characterized by the presence of an unwanted organism.

3. A method of treating a subject for a disorder characterized by the presence of an unwanted organism comprising: administering to the subject, a polycationic photosensitizer conjugate comprising chlorin e6 coupled to polylysine; irradiating the subject with energy of a wavelength appropriate to produce a cytotoxic effect by the photosensitizer; thereby treating the subject, for the disorder characterized by the presence of an unwanted organism.

4. A method of treating a subject for a disorder of the oral cavity characterized by the presence of an unwanted bacterium comprising: administering to the subject, a polycationic photosensitizer conjugate comprising chlorin e6 coupled to polylysine; irradiating the subject with energy of a wavelength appropriate to produce a cytotoxic effect by the photosensitizer; thereby treating the subject, for the disorder characterized by the presence of an unwanted organism.

5. A method of treating a subject, for a disorder characterized by the presence of an unwanted bacterium, comprising: administering to the subject, a polycationic photosensitizer conjugate comprising chlorin e6 coupled to polylysine; providing the subject with irradiation of energy of a wavelength appropriate to produce a cytotoxic effect by the chlorin e6; thereby treating the subject, for the disorder.

* * * * *